United States Patent [19]

Sugerman et al.

[11] Patent Number: 4,657,988
[45] Date of Patent: Apr. 14, 1987

[54] REPOLYMERIZATION

[75] Inventors: Gerald Sugerman, Allendale, N.J.; Salvatore J. Monte, Staten Island, N.Y.

[73] Assignee: Kenrich Petrochemicals, Inc., Bayonne, N.J.

[21] Appl. No.: 834,794

[22] Filed: Feb. 28, 1986

Related U.S. Application Data

[63] Continuation-in-part of Ser. No. 725,437, Apr. 22, 1985, which is a continuation-in-part of Ser. No. 609,727, May 14, 1984, abandoned.

[51] Int. Cl.⁴ ............................................. C08G 63/76
[52] U.S. Cl. ..................................... 525/437; 525/390; 525/444; 525/453; 525/534; 528/17; 528/56; 528/207; 528/279; 528/286; 528/288
[58] Field of Search ............... 525/390, 437, 444, 453, 525/534; 528/17, 56, 207, 279, 286, 288

[56] References Cited

U.S. PATENT DOCUMENTS

| | | | |
|---|---|---|---|
| 4,036,796 | 7/1977 | Sugiyama et al. | 525/437 X |
| 4,115,371 | 9/1978 | Bier et al. | 528/286 X |
| 4,148,989 | 4/1979 | Tews et al. | 525/437 |
| 4,452,970 | 6/1984 | Brunelle | 528/279 |
| 4,454,312 | 6/1984 | Kuze et al. | 528/279 X |
| 4,482,700 | 11/1984 | Kühnrich et al. | 528/279 |

*Primary Examiner*—Lucille M. Phynes
*Attorney, Agent, or Firm*—Bert J. Lewen; Henry Sternberg

[57] ABSTRACT

Polymeric materials are repolymerized by intensely admixing the polymer with an additive having the formula:

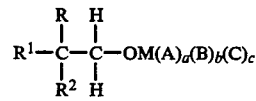

wherein M is titanium or zirconium, R, $R^1$ and $R^2$ are each a monovalent alkyl, alkenyl, alkynyl, aralkyl, aryl or alkaryl group having up to 20 carbon atoms or a halogen or ether substituted derivative thereof, and, in addition, $R^2$ may also be an oxy derivative or an ether substituted oxy derivative of said groups; A, B, and C are each a monovalent aroxy, thioaroxy, diester phosphate, diester pyrophosphate, oxyalkylamino, sulfonyl or carboxyl containing up to 30 carbon atoms; and $a+b+c=3$. The repolymerized polymers have improved physical properties and higher heat distortion temperatures, experience less thermal degradation and show greater solvolysis resistance than the polymers prior to the repolymerization.

5 Claims, No Drawings

REPOLYMERIZATION

RELATED APPLICATIONS

This application is a continuation-in-part of U.S. patent application Ser. No. 725,437, filed Apr. 22, 1985, which is a continuation-in-part of U.S. patent application Ser. No. 609,727, filed May 14, 1984 now abandoned.

BACKGROUND OF THE INVENTION

It has long been desirable to improve the physical properties of a broad range of polymeric materials such as polyalkylene terephthalates, polypropylene oxides, and polyurethanes. These materials frequently suffer from inadequate physical properties, for example, low tensile strength, flexural strength, flexural modulus, notched Izod, or percent elongation. In addition, often the heat distortion temperature is not adequate for certain applications and these polymers suffer thermal degradation, as well as poor resistance to solvents.

BRIEF DESCRIPTION OF THE INVENTION

The subject invention relates to the repolymerization of polymeric materials by intensively admixing such materials with an additive having the formula:

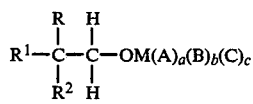

wherein M is titanium or zirconium, R, $R^1$ and $R^2$ are each a monovalent alkyl, alkenyl, alkynyl, aralkyl, aryl or alkaryl group having up to 20 carbon atoms or a halogen or ether substituted derivative thereof, and, in addition, $R^2$ may also be an oxy derivative or an ether substituted oxy derivative of said groups; A, B, and C are each a monovalent aroxy, thioaroxy, diester phosphate, diester pyrophosphate, oxyalkylamino, sulfonyl or carboxyl containing up to 30 carbon atoms; and $a+b+c=3$.

Generally speaking, from 0.005 to 5wt. % of such mixtures should be added to the polymeric material.

While not intending to be limited by any particular theory, it is believed that the process of the subject invention is effective because it allows the polymeric material to continue to polymerize in the direction of thermodynamic equilibrium. By so doing, the molecular weight distribution of the polymer is narrowed, thereby reducing the presence of low molecular weight and very high molecular weight components. Low molecular weight components, because of their solvating action, adversely affect the impact properties and heat distortion properties of the polymer. On the other hand, very high molecular weight components prevent the flow of the polymer and thereby limit its processability.

Where copolymeric materials are treated, the tendency is to randomize block copolymer units. This serves to improve both impact properties and heat distortion, and effectively renders the copolymers more elastomeric and processable. With homopolymers, the process of the invention results in the isomerization of the starting material with respect to vinyl and vinylidene polymerization, increasing the number of head-to-head polymeric units.

A prime application of the instant invention is to upgrade commodity plastics to engineering plastics, that is, plastics having highly advantageous physical properties. Polyolefins such as polyethylene and polypropylene can be admixed with the organo-titanates and zirconates to form ethylene-propylene rubbers. Similarly, if the aforesaid two polymeric materials are further admixed with a polydiene, ethylene-propylene-diene rubbers may be inexpensively produced. Another application with polyolefins is the admixture of polyethylene with polydienes to make crosslinkable polyethylenes useful in coating wire and cable. The aforesaid materials should be processed at temperatures wherein the polymers are liquid, as for example at temperatures from 0° to 450° C. at atmospheric pressure. Other useful applications include the blending of polybutylene terephthalate and polyethylene terephthalate to form random copolymers; and polyethylene with polystyrenics to produce engineering plastics, such as those sold under the trademarks of KRATON (Shell), SOLPRENE (Phillips), and SANTOPRENE (Monstano).

Still further, the homopolymer polypropylene can be rearranged to form a head-to-head polymer such as conventionally obtained by the polymerization of 2-methylpentene-2. Such materials are substantially better than the conventional homopolymer, in that their physical properties and chemical resistance are better than those of their less ordered analogues.

Still further areas of application are the repolymerization of phthalate esters such as polyethylene terephthalate with bisphenol-A esters to make polyarylate liquid crystalline polymers. Such materials are sold commercially for as much as $30 per pound under the trademarks CELON (Celanese) and XIDER (Dartco). Polyarylates may be made with other esters, such as poly-p-hydroxybenzate and phthalate esters. Polyamides and polyesters may be repolymerized to form polyamido-polyester copolymers. Typical starting materials are nylon and polyethylene terephthalate or polybutylene terephthalates. These form very strong moisture resistant polymers. Repolymerizing polyamides with polyurethanes also results in the formation of high impact polyamides.

DETAILED DESCRIPTION OF THE INVENTION

The organo-titanates and organo-zirconates which are within the scope of the formula mentioned above that are particularly preferred in the application of the instant invention are those where $R^1$, $R^2$ or both have an ether oxygen atom beta to the quaternary carbon.

Ar, in th above formulas, may be a monovalent aryl or alkaryl group having from 6 to about 20 carbon atoms, optionally containing up to 3 ether oxygen substituents, and substituted derivatives thereof wherein the substitutions are up to a total of three halogens or amino groups having the formula $NR^8R^9$ wherein $R^8$ and $R^9$ are each hydrogen, an alkyl group having 1 to 12 carbon atoms, an alkenyl group having from 2 to 8 carbon atoms, a cycloalkyl group having from 3 to 12 carbon atoms, and an aryl group having from 6 to 12 carbon atoms; and $R^3$ and $R^4$ may each be the same group as R, $R^1$ and Ar. $R^5$ and $R^6$ may be hydrogen, an alkyl or aminoalkyl group having from 1 to 15 carbon atoms and $R^7$ may be an alkylene group having from 1 to 6 carbon atoms or an arylene group having from 6 to 10 carbon atoms or a combination thereof; and $a+b+c$ is equal to 3.

A wide variety of ligands, subject to the limitations heretofore expressed, may be used in the practice of this invention. The most suitable for a particular application will depend largely upon the polymer system employed and, to a lesser degree, upon the particular curative and/or extenders introduced into such system, if any.

Particularly preferred examples of the R, $R^1$ and $R^2$ groups are alkyl having 1 to 8 carbon atoms; aralkyl having 6 to 10 carbon atoms such as benzyl; the aryl and alkaryl groups having from 6 to 10 carbon atoms including phenyl, naphthyl, tolyl, xylyl; and the halogen-substituted bromophenyl; and the allyloxy-substituted alkyl having from 4 to 20 carbon atoms and the allyloxy-substituted aryl having from 9 to 20 carbon atoms. Where $R^2$ is an oxy derivative, the most preferred compounds are the alkoxy derivatives having from 1 to 3 carbon atoms and the phenoxy group.

Preferred $R^3$ and $R^4$ groups are alkyl groups having 1 to 12 carbon atoms, aryl and alkaryl groups having from 6 to 12 carbon atoms and ether-substituted alkyl having from 3 to 12 carbon atoms.

Examples of specific, R, $R^1$, $R^2$, $R^3$ and $R^4$ groups are: methyl, propyl, cyclohexyl, 2,4-dimethoxybenzyl, 1-methyl-4-acenaphthyl-2-ethyl-2-furyl and methallyl. $R^2$, in addition, may be methoxy, phenoxy, naphthenoxy, cyclohexene-3-oxy, 4-isobutyl-3-methoxy, 1-phenanthroxy and 2,4,6-trimethylphenoxy.

Examples of A, B and C ligands useful in the practice of this invention are likewise numerous. These include aryl and thioaryl ligands such as phenoxy, 2,4-dimethyl-1-naphthoxy, 3-octyl-1-phenanthroxy and 3,5-diethyl-2-thioanthryl and 2-methyl-3-methoxy thiophenyl as well as diester phosphates such as dibutyl, methylphenyl, cyclohexyl, lauryl and bismethoxyethoxyethyl phosphate and their pyrophosphate analogs as well as aryl sulfonyl groups such as phenylsulfonyl, 2,4-dibutyl-1-naphthalene sulfonyl and 2-methyl-3-ethyl-4-phenanthryl sulfonyl.

Particularly effective are carboxyl groups such as acetyl, methacryl, stearyl, 4-phenoxy and 4-phenoxy butyl. Illustrative of the compounds of the instant invention are those listed in Table A:

TABLE A $(CH_3)CCH_2OTi[OC(O)C_{17}H_{35}]_3(CH_3)_2(C_6H_5)CCH_2OTi(OC_6H_5)_2[OC(O)C_6H_5]$ $(CH_3=C(CH_3)CH_2O)_2(C_2H_5)_2CCH_2OTi[SC_6H_4-N-OC_2H_5]_2[OC_6H_4C(CH_3)_2C_6H_5]$ $(C_6H_{11}O)(iso-C_{12}H_{25})_2CCH_2OTi[OS(O)_2C_6H_4C_{12}H_{25}]_3$ $(CH_2=CHCH_2O)(C_3H_7)(C_2H_5)CCH_2Ti[OP(O)(OC_4H_9)OP(O)(OH)OC_4H_9)]_3$ $(CH_3)(HC=CCH_2O)(C_6H_5)CCH_2OTi[OP(O)(OC_2H_4OCH_3)](OCH_3)[OC_6H_4-p-C_2H_5]$ $(C_6H_{11})(iso-C_3H_7)(C_4H_9O)CCH_2OTi[S(O)_2C_6H_4-O-CH_3][SC_6H_5]_2$ $(CH_3)(C_6H_5CH_2O)(C_2H_5)CCH_2OTi[OP(O)(OC_6H_4-p-CH_3)(O)(C_2H_4OCH_3)][OP(O)(OH)OP(O)(OC_3H_7)_2]_2$ $(C_2H_5)(C_3H_7)(CH_2=CHO)CCH_2Ti[OC(O)-neo-C_9H_{17}]_3$ $[C(CH_3)_2=C(C_6H_5)OCH_2]_2(iso-C_3H_7)CCH_2OTi[OC_{10}H_7][OC(O)CH_2CH_3]_2$ $(C_2H_5OCH_2)(CH_3)(C_6H_5)CCH_2OTi[OC_2H_4NHCH_3]$ $(CH_3)_2(C_4H_9)CCH_2OTi[OC_3H_6N(C_6H_5)C_4H_8C_{10}H_7]_2[OC(O)CH_3]$ $(C_6H_5)_2(CH_3O)CCH_2OZr[OC(O)C_9H_{19}-neo]_3$ $(C_{10}H_7S)(C_3H_5)(C_2H_5)CCH_2OZr(OC_6H_4Cl)[SC_6H_3CCH_3)_2](OS(O)_2C_{10}H_9-2)$ $(CH_3)_2(C_5H_{11}O)CCH_2OZr[SC_6H_4C(CH_3)_2C_6H_5]_3$ $(CH_2=CH)_2(CH_3OCH_2)CCH_2OZr[OP(O)(OC_6H_5Br)_2][OP(O)(OCH_3)OP(O)(OCH_3)(OH)]_2$ $(C_3H_7OCH_2O)(C_2H_5)(CH_3)CCH_2OZr[OC_6H_5]_3$ $(CH_3)_3CCH_2OZr[OC(O)CH_3][OP(O)(OC_5H_9)(OCH_2C_6H_7CH_3)][OS(O)_2C_6H_3(Cl)(Br)(CH_3)-1,2,3]$ While a wide variety of polymers may be treated with the neoalkoxy compounds of the invention, the admixture thereof are particularly useful with engineering plastics, which are conventionally processed between 200° and 400° C. The organo-titanates of the prior art were not satisfactory in this application, because of their lack of stability. It should be understood, however, that the neoalkoxy compounds may also be blended with other resins such as PVC and used in paint and other coating applications, in the latter cases because of the solvent stability of these compounds.

Broadly, from 0.005 to 5 wt. % of the neoalkoxy compounds are added to the resin, preferably from 0.1 to 1.0%. If the amount of the neoalkoxy compound added is greater than that needed to affect the surface properties of the resin, the neoalkoxy compounds will have a plasticizing effect on the resin.

The optimum amount of the neoalkoxy compounds added to the resins may be readily determined by those skilled in the art by consideration of the examples set forth herein and by simple experimentation. By so proceeding, the desired flow properties for a particular resin can be reasily achieved.

Examples of the engineering plastics which may be admixed with neoalkoxy compounds include epoxy resins, fluorocarbons, modified phenylene oxides, nylons, polyethylene terephthalate, polybutylene terephthalate, phenolics, polyamides, polycarbonates, polyetheretherketones, polyaryletherketones, polyether imides, polyphenylene sulfides, polysulfones, polyarylsulfones, styrene, polyester copolymers, styrenics, such as, polystyreneacrylonitrile-butadiene-styrene, styrene-actylonitrile, styrene-butadiene, and styrene-maleic anhydride copolymers.

The neoalkoxy compounds also improve the dimensional stability of shaped resins. This is reflected by reduced water absorption in humid environments, and is amply demonstrated by the examples hereinafter set forth. Other positive effects in certain filled plastics include improved conductivity, a reflection of the improved dispersion of the conductive filler in the polymer; flame retardancy, a result of the exclusion of air from the interstices of the resin and better filler dispersion; less heat distortion; and catalytic effects. Data for all of these effects are given in the examples which follow.

The solvent stability of the neoalkoxy compounds, as mentioned previously, is also a marked advantage over the prior art. The prior art hydroxyzable groups reacted with many solvents, thereby destroying the efficacy of the organo-titanate as a coupling agent. Examples of solvents which quickly deactivated the prior art coupling agents are protonated solvents, such as hydroxylated polymers, vicinal glycols (both monomeric and polymeric), solvents which exhibit keto-enol tautomerism, organic acids, esters, isocyanates and carboxylates. In the case of the neoalkoxy compounds of the invention, however, they are substantially non-reactive at the processing temperatures of most polymeric materials.

The resistance to protonated solvents, accordingly, improves the shelf stability of polymeric compositions containing the neoalkoxy compounds. Rather than being useful for just minutes after blending with the resin, stability can now be extended for weeks. Actually, this is of substantial advantage in using the organo-titanates or organo-zirconates of the invention as coupling agents, rather than the conventional primary, secondary and tertiary alkoxy-type.

The reaction product of the neoalkoxy compounds and fillers are a further embodiment of the instant invention. Generally speaking at least 0.01 part, preferably from 0.1 to 5 parts by weight of the neoalkoxy compound are used to treat each 100 parts of filler. Most preferable is the reaction of from 0.2 to 2 parts per 100 parts of filler.

Reaction is facilitated by admixing under the proper conditions. Optimum results depend on the properties of the alkoxy compound, namely, whether it is a liquid or solid, and its decomposition and flash points. The particle size, the geometry of the particles, the specific gravity, the chemical composition, among other things, must be considered. Additionally, the treated inorganic material must be thoroughly admixed with the polymeric medium. The appropriate mixing conditions depend on the type of polymer, whether it is thermoplastic or thermosetting, its chemical structure, etc., as will be readily understood by those skilled in the art.

Where the inorganic material is pretreated with the organic titanate or zirconate, it may be admixed in any convenient type of intensive mixer, such as a Henschel or Hobart mixer or a Waring blender. Even hand mixing may be employed. The optimum time and temperature are determined to obtain substantial reaction between the inorganic material and the organic metalate. Mixing is performed under conditions at which the organic metalate is in the liquid phase, at temperatures below the decomposition temperature. While it is desirable that the bulk of the hydrolyzable groups be reacted in this step, this is not essential where the materials are later admixed with a polymer, since the substantial completion of the reaction may take place in this latter mixing step.

Polymer processing, e.g., high shear mixing, is generally performed at a temperature well above the second order transition temperature of the polymer, desirably at a temperature where the polymer will have a low melt viscosity. For example, low density polyethylene is best processed at a temperature range of 170° to 230° C.; high density polyethylene from 200° to 245° C.; polystyrene from 230° to 260° C.; polypropylene from 230° to 290° C.; thermoplastic polyesters from 260° to 280° C.; polyamides from 260° to 320° C. and polycarbonates from 230° to 255° C. Temperatures for mixing other polymers are known to those skilled in the art and may be determined by reference to existing literature.

In order to further illustrate the subject invention, the following examples are provided. Examples A to C show the preparation of typical neoalkoxy compounds. The subsequent examples show the process and products of the invention.

EXAMPLE A

Titanium IV 2,2-Dimethyl Propanolato, Tris(Dioctyl)Phosphateo-O

To a glass vessel equipped with a mechanical agitator, external heating and cooling, vapor condensation means, a distillate trap and off-gas scrubber was added one mole of 2,2-dimethylpropanol and three moles of dioctyl hydrogen phosphate as well as two liters of mixed isomer xylene. The reactor was flushed with nitrogen and maintained under a slow nitrogen purge during the addition of one mole of titanium tetrachloride over a period of two hours. External heating and cooling was supplied, as necessary, to maintain the operating temperature in the range of 45°–60° C. After the addition of the titanium tetrachloride, nitrogen purge was slightly accelerated for an additional two hours followed by evaporation of the reaction mixture in vacuo to produce a bottoms fraction boiling above 150° C. Elemental analysis of the moderately viscous red-brown residual oil was consistent with its formulation as $C_5H_{11}Ti[OP(O)(OC_8H_{17})_2]$. The off-gas scrubber contents were analyzed to show that approximately 4 moles of hydrogen chloride had been captured in the caustic scrubber solution. Subsequent high pressure liquid chromatography (HLPC) analysis of a portion of bottoms product was used to determine product yield employing a Fourier transform infrared detector system (FTIR) for quantification of effluent assay. Results for the above preparation and for those producing analogous products by similar means from titanium tetrachloride together with the product yields are shown in Table A. The Code in the lefthand column of the table is to designate these products in subsequent examples:

TABLE A

| Code | Raw Materials | Product Structure | Yield (mole %) via HLPC/FT-IR |
|---|---|---|---|
| A | $(CH_3)_3CCH_2OH$<br>$3HOP(O)(OC_8H_{17})_2$ | $(CH_3)_3CCH_2OTi[OP(O)(OC_8H_{17})_2]_3$ | 87 |
| B | $(CH_3)_3CCH_2OH$<br>$3HOC_6H_5$ | $(CH_3)_3CCH_2OTi(OC_6H_5)_3$ | 92 |
| C | $(CH_2=CHCH_2OCH_2)_2(C_2H_5)CCH_2OH$<br>$3HOC(O)neo-C_9H_{19}$ | $(CH_2=CHCH_2OCH_2)_2(C_2H_5)CCH_2OTi$<br>$[OC(O)neo-C_9H_{19}]_3$ | 90 |
| D | $(C_6H_5)(CH_3OCH_2)(CH_3)CCH_2OH$<br>$3HOS(O)_2C_6H_4C_{12}H_{25}$ | $(C_6H_5)(CH_3OCH_2)(CH_3)CCH_2OTi$<br>$(OS(O)_2C_6H_4C_{12}H_{25})_3$ | 87 |
| F | $(C_{10}H_7-1-O)(C_2H_5)_2CCH_2OH$<br>$3HSC_6H_4-1-OCH_3$ | $(C_{10}H_7-1-O)(C_2H_5)_2CCH_2OTi$<br>$(SC_6H_4-1-OCH_3)_3$ | 92 |
| G | $(CH_3O)(C_6H_5)(iso-C_8H_{17})CCH_2OH$<br>$3(HO)_2(C_4H_9O)CH_3O)P_2O_3$ | $(CH_3O)(C_6H_5)(iso-C_8H_{17})CCH_2OTi$<br>$[OP(O)(OH)OP(O)(OC_4H_9)(OCH_3)]_3$ | 84 |

The empirical formula, the calculated and analysed values for certain of the above products are as follows:

| Code | Calculated for C/H/Ti | Found for C/H/Ti |
|---|---|---|
| A | $C_{49}H_{113}O_{13}P_3Ti$—60.6/11.1/4.58 | 60.4/10.9/4.63 |

-continued

| Code | Calculated for C/H/Ti | Found for C/H/Ti |
|------|----------------------|------------------|
| B | $C_{23}H_{26}O_4Ti$—66.7/6.28/11.6 | 66.8/6.19/11.7 |
| C | $C_{43}H_{78}O_9Ti$—65.6/9.92/6.11 | 65.7/9.98/6.21 |
| G | $C_{32}H_{66}O_{23}P_6Ti$—36.5/6.27/4.56 | 36.7/6.18/4.51 |

EXAMPLE B

Preparation of Titanium IV 2-Methyl,2-Phenylbutanolato,Bis(Dibutyl) Phosphato-O,(Dioctylphenyl)Pyrophosphato-O A reactor such as that described in Example A was charged with one mole of titanium IV tetrabutoxide. Temperature was adjusted to 50° C. and maintained between 50° C. and 70° C. by external heating and cooling and reactor pressure held at 10 mm of Hg. during the addition, sequentially, of one mole of 2-methyl-2-phenylbutanol (20 minutes), two moles of dibutyl pyrophosphate (1 hour, 5 minutes), and one mole of dioctylphenyl pyrophosphate (1 hour, 45 minutes).

During the addition, the distillate was collected and determined by gas liquid chromatography to be essentially pure butanol totaling 3.84 moles. The residual reaction product was analyzed by HLPC/FTIR as described in Example A. Results of this experiment and of several products made by analogous means are shown in Table B on a per mole of titanium tetralkoxide basis:

The empirical formula, the calculated and analysed values for certain of the above compounds are as follows:

| Code | Calculated for C/H/Ti | Found for C/H/Ti |
|------|----------------------|------------------|
| B | $C_{23}H_{26}O_4Ti$—60.6/11.1/4.58 | 60.7/11.3/4.62 |
| K | $C_{44}H_{126}O_{24}P_6Ti$—41.5/9.91/3.77 | 41.6/9.82/3.75 |
| L | $C_{43}H_{64}O_4S_2Ti$—68.3/8.47/6.35 | 68.3/8.39/6.41 |
| M | $C_{49}H_{138}O_{23}P_6Ti$—44.3/10.4/3.61 | 44.1/10.3/3.56 |
| N | $C_{44}H_{123}O_{14}P_3Ti$—60.9/14.2/5.54 | 60.6/14.1/5.58 |
| P | $C_{40}H_{48}O_{10}S_3Ti$—57.7/5.77/5.77 | 57.6/5.84/5.69 |

EXAMPLE C

Production of Neoalkoxy Titanium VI Salts from Titanium IV Salts and Titanium Tetrakis Neoalkoxylates One mole of titanium IV tetrakis(2-allyloxymethyl, 2-propanolato methyl-1-)butanolato was added over a period of two hours to 3 moles of titanium IV tetrakis(-dioctyl)pyrophosphato-O contained in 1 liter of toluene. The reaction mixture was agitated and maintained at 75±5° C. during the addition and for 24 hours after by external heating and cooling. FTIR analysis of HLPC effluents as described in Example 1 (after toluene evaporation in vacuo) indicated that a 73 mole % yield of titanium IV (2-allyloxymethyl, 2-n-propanolatomethyl-1-)butanolato, tri(dioctyl)pyrophosphato-O was obtained. Similarly, isostearate, phosphate and amino analogs were prepared as shown in Table C.

TABLE B

| Code | Raw Materials | Product Structure | Yield (mole %) via HLPC/FT-IR |
|------|--------------|-------------------|-------------------------------|
| H | $(CH_3)(C_6H_5)(C_2H_5)CCH_2OH$<br>$2HOP(O)(OC_4H_9)_2$<br>$(HO)_2(C_8H_{17}C_6H_4O)_2P_2O_3$ | $(CH_3)(C_6H_5)(C_2H_5)CCH_2OTi$<br>$[OP(O)(OC_4H_9)_2]_2$<br>$[OP(O)(OH)OP(O)(OC_6H_{17}C_8H_{17})_2]$ | 71 |
| J | $(CH_2=CHCH_2OCH_2)_2(C_2H_5)CCH_2OH$<br>$HOC(O)iso-C_{17}H_{35}$<br>$2HOS(O)_2C_6H_4C_{12}H_{25}$ | $(CH_2=CHCH_2OCH_2)_2(C_2H_5)CCH_2OTi$<br>$[OC(O)iso-C_{17}H_{35}]$<br>$[OS(O_2)C_6H_4C_{12}H_{25}]_2$ | 62 |
| B | $(CH_3)_3CCH_2OH$<br>$3HOC_6H_5$ | $(CH_3)_3CCH_2OTi(OC_6H_5)_3$ | 96 |
| K | $(CH_2=CHCH_2OCH_2)_2(C_2H_5)CCH_2OH$<br>$3(HO)_2(C_8H_{17}O)_2P_2O_3$ | $(CH_2=CHCH_2OCH_2)_2(C_2H_5)$<br>$CCH_2OTi[OP(O)(OH)OP(O)(OC_8H_{17})_2]_3$ | 85 |
| L | $(CH_3O)(C_4H_9)(C_6H_5)CCH_2OH$<br>$HOC(O)CH_3$<br>$2HSC_6H_4C_8H_{17}$ | $(CH_3O)(C_4H_9)(C_6H_5)CCH_2OTi[OC(O)CH_3]$<br>$[SC_6H_4C_8H_{17}]_2$ | 75 |
| M | $(CH_2=CHCH_2OCH_2)(C_8H_{17}OCH_2)$<br>$(C_2H_5)CCH_2OH$<br>$3(HO)_2(C_8H_{17}O)_2P_2O_3$ | $(CH_2=CHCH_2OCH_2)(C_8H_{17}OCH_2)(C_2H_5)$<br>$CCH_2OTi[OP(O)(OH)OP(O)(OC_8H_{17})_2]_3$ | 63 |
| N | $(CH_2=CHCH_2OCH_2)_2(C_2H_5)$<br>$CCH_2OH$<br>$3HOP(O)(OC_8H_{17})_2$ | $(CH_2=CHCH_2OCH_2)_2(C_2H_5)CCH_2OTi$<br>$[OP(O)(OC_8H_{17})_2]_3$ | 74 |
| P | $neo-C_{10}H_{21}OH$<br>$2\ HOS(O)_2C_{10}H_6-3-CH_3$<br>$HOS(O)_2C_6H_5-p-C_2H_5$ | $neo-C_{10}H_{21}OTi[OS(O)_2C_{10}H_6-3-CH_3]_2$<br>$[OS(O)_2C_6H_4-p-C_2H_5]$ | 61 |

TABLE C

| Code | Raw Materials | Product Structure | Yield (mole %) via HLPC/FT-IR |
|------|--------------|-------------------|-------------------------------|
| Q | $(C_2H_5)(C_3H_7OCH_2)(CH=CHCH_2OCH_2CCH_2O)]_4Ti$<br>$3Ti[OP(O)(OH)OP(O)(OC_8H_{17})_2]_4$<br>$[OP(O)(OC_8H_{17})OP(O)(OH)(OC_8H_{17})]$ | $(C_2H_5)(C_3H_7OCH_2)(CH_2=CHCH_2OCH_2)$<br>$CCH_2OTi[OP(O)(OH)OP(O)(OC_8H_{17})_2]_3$ | 73 |
| R | $[(C_2H_5)(C_3H_7OCH_2)(CH_2=CHCH_2)CH_2)CCH_2OTi_3$<br>$3Ti[OC(O)iso-C_{17}H_{35}]_4$ | $(C_2H_5)(C_3H_7OCH_2)(CH_2CHCH_2OCH_2)$<br>$CCH_2OTi[OC(O)iso-C_{17}H_{35}]_3$ | 79 |
| S | $[(C_2H_5)(C_3H_7OCH_2)(CH_2=CHCH_2OCH_2)CCH_2O]Ti$<br>$3Ti[OP(O)(OC_8H_{17})_2]_4$ | $(C_2H_4)(C_3H_7OCH_2)(CH_2=CHCH_2OCH_2)$<br>$CCH_2OTi[OP(O)(OC_8H_{17})_2]_3$ | 83 |
| T | $[(C_6H_5CH_2)_2(C_6H_5)CCH_2O]_4Ti3Ti[OP(O)(CH_3C_6H_4O)_2]_4$ | $(C_6H_5CH_2)(C_6H_5)CCH_2OTi$<br>$[OP(O)(OC_6H_4CH_3)]_3$ | 71 |

TABLE C-continued

| Code | Raw Materials | Product Structure | Yield (mole %) via HLPC/FT-IR |
|---|---|---|---|
| U | $[(CH_2=CHCH_2OCH_2)_2(C_2H_5)CCH_2O]_4Ti$ $3Ti[OC_2H_4NHC_2H_4NH_2]_4$ | $(CH_2=CHCH_2OCH_2)_2(C_2H_5)CCH_2OTi$ $[OC_2H_4NHC_2H_4NH_2]_3$ | 70 |
| V | $[(CH_2=CHCH_2OCH_2)_2(C_2H_5)CCH_2]_4Ti$ $3Ti[OS(O)_2C_6H_4C_{12}H_{25}]_4$ | $(CH_2=CHCH_2OCH_2)_2(C_2H_5)CCH_2OTi$ $(OS(O)_2C_6H_4C_{12}H_{25})_3$ | |
| W | $[(CH_2=CHCH_2OCH_2)_2(C_2H_5)CCH_2]_4Ti$ $3Ti[OC_6H_4NH_2]_4$ | $(CH_2=CHCH_2OCH_2)_2(C_2H_5)CCH_2OTi$ $(OC_6H_4NH_2)_3$ | |
| Z1 | $[(CH_2=CHCH_2OCH_2)_2(C_2H_5)CCH_2]_4Zr$ $3Zr[OC(O)C_9H_{19}]_4$ | $(CH_2=CHCH_2OCH_2)_2(C_2H_5)CCH_2OZr$ $(OC(O)C_9H_{19})_3$ | |
| Z2 | $[(CH_2=CHCH_2OCH_2)_2(C_2H_5)CCH_2]_4Zr$ $3Zr[OC_6H_4NH_2]_4$ | $(CH_2=CHCH_2OCH_2)_2(C_2H_5)CCH_2OZr$ $(OC_6H_4NH_2)_3$ | |
| Z3 | $[(CH_2=CHCH_2OCH_2)_2(C_2H_5)CCH_2]_4Zr$ $3Zr[OP(OC_8H_{17})_2]_4$ | $(CH_2=CHCH_2OCH_2)_2(C_2H_5)CCH_2OZr$ $(OP(OC_8H_{17})_2)_3$ | |
| Z4 | $[(CH_2=CHCH_2OCH_2)_2(C_2H_5)CCH_2]_4Zr$ $3Zr[(OP(O)(OH)OP(O)(OC_8H_{17})_2]_4$ | $(CH_2=CHCH_2OCH_2)_2(C_2H_5)CCH_2OZr$ $(OP(O)(OH)OP(O)(OC_8H_{17})_2)_3$ | |
| Z5 | $[(CH_2=CHCH_2OCH_2)_2(C_2H_5)CCH_2]_4Zr$ $3Zr[OC_2H_4NHC_2H_4NH_2]_4$ | $(CH_2=CHCH_2OCH_2)_2(C_2H_5)CCH_2OZr$ $(OC_2H_4NHC_2H_4NH_2)_3$ | |
| Z6 | $[(CH_2=CHCH_2OCH_2)_2(C_2H_5)CCH_2]_4Zr$ $3Zr[OC_6H_4NH_2]_4$ | $(CH_2=CHCH_2OCH_2)_2(C_2H_5)CCH_2OZr$ $(OC_6H_4NH_2)_3$ | |

The calculated and analysed values for certain of the above compounds are as follows:

| Code | Calculated for C/H/Ti | Found for C/H/Ti |
|---|---|---|
| Q | $C_{44}H_{128}O_{24}P_6Ti$—41.4/10.0/3.77 | 41.5/10.3/3.84 |
| R | $C_{66}H_{128}O_9Ti$—73.2/11.8/4.44 | 73.0/11.6/4.38 |
| S | $C_{44}H_{125}O_{14}P_3Ti$—60.8/14.4/5.52 | 60.6/14.7/5.59 |
| U | $C_{24}H_{54}O_6N_6Ti$—50.5/9.47/8.42 | 50.3/9.59/8.56 |

The following codes are used to designate analogs of the neoalkoxy titanates for comparative purposes:

| COMPOUND | CODE |
|---|---|
| $i\text{-}C_3H_7OTi[OP(O)(OC_8H_{17})_2]_3$ | AA |
| $n\text{-}C_8H_{17}OTi[OP(O)(OC_8H_{17})_2]_3$ | AB |
| $(2\text{-}C_2H_5)C_6H_{12}OTi[OP(O)(OC_8H_{17})_2]_3$ | AC |
| $i\text{-}C_3H_7OTi[OC(O)neo\text{-}C_9H_{19}]_3$ | AD |
| $C_6H_5CH_2OTi[OC(O)neo\text{-}C_9H_{19}]_3$ | AE |
| $(CH_3OC_2H_4O)_3SiCH=CH_2$ | AF |
| $i\text{-}C_3H_7OTi[OC(O)iso\text{-}C_{17}H_{35}]_3$ | AG |
| $(CH_3OC_2H_4O)_3SiCH_3$ | AH |
| $C_3H_7OTi[OP(O)(OH)OP(O)(OC_8H_{17})_2]_3$ | AJ |
| $C_8H_{17}OTi[OP(O)(OH)OP(O)(OC_8H_{17})_2]_3$ | AK |
| $i\text{-}C_3H_7OTi[OS(O)_2C_6H_4C_{12}H_{25}]_3$ | AL |
| $C_6H_5CH_2OTi[OS(O)_2C_6H_3(CH_3)_2]_3$ | AM |
| $(CH_3O)_3SiC_3H_6SH$ | AN |
| $(i\text{-}C_3H_7O)Ti[OC_6H_4C(CH_3)_2C_6H_5]_3$ | AO |
| $(C_2H_5O)_3SiC_3H_6NH_2$ | AP |
| $(i\text{-}C_3H_7O)Ti[OC_2H_4NHC_2H_4NH_2]_3$ | AQ |
| $(CH_3O)_3SiC_6H_5$ | AR |
| $(CH_3O)_3SiC_3H_6NHC_2H_4NH_2$ | AS |
| $(C_8H_{17})Ti[OC_6H_4C(CH_3)_2C_6H_5]_3$ | AT |
| $(i\text{-}C_3H_7O)Ti[OC(O)C_7H_{15}]_3$ | AU |
| $(CH_3O)SiC_3H_6OCH_2CH\text{---}CH_2$ | AV |

EXAMPLE 1

Filled and Unfilled Polybutylene Terephthalate

Formulations were prepared by batch tumble blending of the appropriate proportions of PBT (Gafite 1600A, GAF Corp.) and mica (Suzerite-Martin Marietta) together with 0.3 wt. % of additive by weight of mica content in a double cone type blender prior to extrusion in a 24:1 NRM two stage vented extruder at approximately $250 \pm 10°$ C. with a virtually flat temperature profile. Test samples were injection molded at 240° C. and annealed for 48 hrs. at 100° C. prior to test. Results are given in Table 1:

TABLE 1

| Additive | % Mica | Tensile MPa ASTM D638 | Flexural Strength at Yield MPa ASTM D638 | Flexural Modulus GPa ASTM D790 | Notched Izod KJ/M ASTM D256 | % Elongation ASTM D638 |
|---|---|---|---|---|---|---|
| None | None | 69 | 83 | 2.3 | 1.0 | 260 |
| C | " | 74 | 91 | 2.5 | 1.5 | 360 |
| J | " | 71 | 87 | 2.4 | 1.3 | 340 |
| N | " | 78 | 89 | 2.2 | 1.4 | 350 |
| T | " | 74 | 83 | 2.4 | 1.3 | 340 |
| AA | " | 67 | 80 | 1.6 | 1.4 | 250 |
| AT | " | 65 | 77 | 1.5 | 1.6 | 340 |
| AR | " | 69 | 81 | 2.0 | 1.1 | 240 |
| None | 30 | 81 | 121 | 8.2 | 0.1 | 3 |
| C | 30 | 84 | 127 | 9.1 | 0.6 | 16 |
| J | 30 | 86 | 129 | 9.3 | 0.7 | 35 |
| N | 30 | 84 | 126 | 9.0 | 0.5 | 20 |
| T | 30 | 89 | 124 | 8.6 | 0.5 | 30 |
| AA | 30 | 78 | 117 | 7.8 | 0.2 | 4 |
| AT | 30 | 80 | 115 | 7.6 | 0.2 | 5 |
| AR | 30 | 79 | 116 | 7.9 | 0.2 | 3 |
| None | 50 | 82 | 124 | 10.2 | 0.07 | 2 |
| C | 50 | 85 | 129 | 10.8 | 0.25 | 11 |
| J | 50 | 84 | 147 | 10.7 | 0.40 | 8 |
| N | 50 | 84 | 147 | 10.9 | 0.40 | 6 |
| T | 50 | 86 | 148 | 10.0 | 0.30 | 7 |

TABLE 1-continued

| Additive | % Mica | Tensile MPa ASTM D638 | Flexural Strength at Yield MPa ASTM D638 | Flexural Modulus GPa ASTM D790 | Notched Izod KJ/M ASTM D256 | % Elongation ASTM D638 |
|---|---|---|---|---|---|---|
| AA | 50 | 80 | 135 | 9.9 | 0.10 | 2.5 |
| AT | 50 | 81 | 137 | 9.9 | 0.10 | 2.5 |
| AR | 50 | 80 | 133 | 9.6 | 0.10 | 1.5 |

Note that in each and every instance, the products of the instant invention had superior overall properties as compared to those of the prior art.

EXAMPLE 2

Injection Molded PPO

Modified polyphenylene oxide (Noryl N-300—General Electric Co.) pellets were tumble blended with additive in a pneumatic conveyer system and screw injection molded at 270° C. to product test specimens. The results of independent additions of various additives (at 0.3 wt. %) are given in Table 2:

TABLE 2

| Additive | Tensile MPa ASTM D638 | Flexural Modulus GPa ASTM D790 | % Elongation ASTM D638 | Notched Izod KJ/M ASTM D256 | Heat Distortion Temp 1.81 MPa ASTM D648 |
|---|---|---|---|---|---|
| None | 83 | 4.0 | 15 | 0.16 | 150 |
| M | 89 | 4.1 | 84 | 0.29 | 150 |
| N | 94 | 3.8 | 90 | 0.34 | 148 |
| K | 82 | 4.4 | 72 | 0.43 | 152 |
| H | 83 | 4.2 | 61 | 0.45 | 154 |
| AB | 77 | 3.7 | 18 | 0.18 | 141 |
| AK | 79 | 3.5 | 20 | 0.22 | 137 |
| AP | 68 | 3.3 | 16 | 0.30 | 143 |
| AS | 81 | 3.7 | 15 | 0.25 | 146 |
| AT | 80 | 3.8 | 21 | 0.15 | 141 |

Note that the products of the instant invention, when employed as minor additives in PPO injection molding, not only provided superior elongation and impact improvement as compared to the prior art, but simultaneously gave less heat distortion temperature loss than did the prior art analogs.

EXAMPLE 3

Polyethylene and Polybutylene Terephthalate Alloy

Blends of 50 parts of polyethylene terphthalate (Tenite 6857—Eastman), 48 parts of polybutylene terephthalate (Gafite 1600-A—GAF), 2 parts of titanium dioxide (R-901—Dupont), and 0.12 parts of the specified additive were extruded in a single stage 24:1, L:D Prodox extruder at 275°–305° C. followed by injection molding of physical test specimens at 300° C. in a ram type molding unit. A control test specimen was also prepared by melt blending in a nitrogen blanketed autoclave. The results of these evaluations are given in Table 3:

TABLE 3

| Additive | Intrinsic Viscosity (poise) | Melt Flow Index ASTM D1238 | Notched Izod KJ/M ASTM D256 |
|---|---|---|---|
| None Melt Blend | 2.38 | 3.2 | 0.02 |
| None Extruded | 2.11 | 3.8 | 0.04 |
| J | 2.48 | 4.2 | 0.14 |
| R | 2.46 | 4.5 | 0.16 |
| T | 2.50 | 4.1 | 0.18 |
| AA | 2.21 | 3.7 | 0.07 |
| AN | 2.33 | 3.8 | 0.07 |
| AR | 2.09 | 3.7 | 0.06 |
| AM | 2.11 | 3.8 | 0.06 |

The experimental results tabulated in Table 27 clearly demonstrate that the products of the instant invention minimize thermal degradation of PBT/PET alloy far more effectively than do prior art analogs which have previously been shown to be effective process aids at lower temperatures.

EXAMPLE 4

Polyurethane

This example demonstrates the superior thermal/solvolytic stability of the products of the instant invention as compared to those of the prior art with respect to polyester polyurethanes (Pellethane 2102-80HE—Upjohn) when employed in both casting and extrusion modes. For extrusion evaluation, the components were tumble blended with 0.4% additive and extruded at 205°–220° C. using a two stage vented 24:1 Prodox extruder; followed by injection molding of test specimens at 210° C.

Casting was accomplished by dissolving the resin in anisole at ambient temperature to produce a 20% solution containing 0.5% additive followed by solvent evaporating (after appropriate aging) in vacuo at 80° C. to produce castings from which test samples were die cut for evaluation. Results are given in Table 4A and 4B, respectively:

TABLE 4A

| | EXTRUDED THERMOPLASTIC POLYESTER POLYURETHANE | | | |
|---|---|---|---|---|
| Additive | Tensile MPa ASTM D638 | % Elongation ASTM D638 | Flexural Modulus GPa ASTM D790 | Hardness Shore A |
| None | 45 | 550 | 0.05 | 83 |
| U | 58 | 480 | 0.22 | 87 |
| T | 48 | 540 | 0.12 | 84 |
| B | 46 | 550 | 0.13 | 84 |
| AQ | 41 | 590 | 0.05 | 83 |
| AT | 40 | 550 | 0.05 | 83 |
| AR | 44 | 510 | 0.05 | 82 |

Note the products of the instant invention provide enhancement of flexural modulus when used as additives in extruded polyester polyurethane, whereas their non-neoanalogs are ineffective.

TABLE 4B
CAST POLYESTER POLYURETHANE

| Additive | Aging Time Hr. | Tensile MPa ASTM D638 | % Elongation ASTM D638 | Flexural Modulus GPa ASTM D790 | Hardness Shore A |
| --- | --- | --- | --- | --- | --- |
| None | 0.1 | 48 | 600 | 0.05 | 83 |
| None | 168 | 48 | 600 | 0.05 | 82 |
| U | 0.1 | 61 | 580 | 0.31 | 88 |
| U | 168 | 60 | 570 | 0.29 | 88 |
| T | 0.1 | 52 | 600 | 0.13 | 83 |
| T | 168 | 52 | 600 | 0.12 | 83 |
| B | 0.1 | 54 | 600 | 0.15 | 83 |
| B | 24 | 50 | 600 | 0.11 | 83 |
| B | 168 | 50 | 600 | 0.09 | 83 |
| AQ | 0.1 | 50 | 600 | 0.09 | 88 |
| AQ | 24 | 49 | 600 | 0.05 | 83 |
| AT | 0.1 | 51 | 600 | 0.08 | 82 |
| AT | 24 | 47 | 600 | 0.05 | 82 |
| AR | 0.1 | 50 | 600 | 0.10 | 83 |
| AR | 24 | 50 | 600 | 0.04 | 82 |

Note the products of the instant invention enhance the properties of cast polyester polyurethane in anisole solution for at least 168 hrs., whereas their prior art analogs failed within one-seventh of said period. This demonstrates the superior solvolysis resistance of the products of the instant invention.

EXAMPLE 5

Thermoplastic Urethane

The addition of 0.3% neoalkoxy compounds on the physical properties of thermoplastic urethane extrusion profiles is shown in the following table.

TABLE 5

| Additive | Elongation at Break % | Tensile Strength at Break (MPa) |
| --- | --- | --- |
| None | 640 | 35 |
| C | 780 | 35 |
| V | 810 | 39 |
| N | 760 | 42 |
| K | 650 | 45 |
| U | 600 | 52 |
| Z5 | 620 | 50 |
| Z6 | 580 | 55 (DC) |

(DC) Severe Discoloration

The above table shows that, generally speaking, the elongation to break is improved most markedly by the neoalkoxy titanates, while the tensile strength of the material is improved to the greatest extent by the neoalkoxy zirconates.

EXAMPLE 6

Chlorinated Polyvinyl Chloride

Samples of chlorinated polyvinyl chloride (Geon 88935) were high shear blended with 0.2 wt. % additive prior to injection molding at 210° C. Results are given in Table 6.

TABLE 6

| Additive | Tensile MPa ASTM D638 | % Elongation ASTM D638 | Flexural Modulus GPa ASTM D790 | Notched Izod KJ/M ASTM D257 |
| --- | --- | --- | --- | --- |
| None | 53 | 180 | 28 | 0.4 |
| A | 55 | 230 | 27 | 0.8 |
| G | 61 | 240 | 23 | 0.7 |
| J | 58 | 210 | 25 | 0.7 |
| K | 60 | 250 | 28 | 0.8 |
| M | 56 | 210 | 27 | 0.5 |
| N | 52 | 190 | 29 | 0.5 |

TABLE 6-continued

| Additive | Tensile MPa ASTM D638 | % Elongation ASTM D638 | Flexural Modulus GPa ASTM D790 | Notched Izod KJ/M ASTM D257 |
| --- | --- | --- | --- | --- |
| AJ | 46 | 200 | 22 | 0.4 |
| AA | 45 | 170 | 25 | 0.5 |
| AL | 42 | 190 | 25 | 0.5 |
| AR | 50 | 200 | 24 | 0.3 |
| AP | 50 | 160 | 28 | 0.3 |

Note that the products of the instant invention provided superior impact properties as compared to those imparted by prior art products.

EXAMPLE 7

Acrylonitrile-Styrene-Butadiene

Samples of precompounded acrylonitrile-styrene-butadiene copolymer (Cycolac KJM, Borg-Warner) were tumble blended in a drum tumbler with 0.2 wt. % of additive and thereafter injection molded at 270° C. Flame retardancy improvement is shown in Table 7.

TABLE 7

| Additive | Flame Retardant Rating UL-94 | | |
| --- | --- | --- | --- |
| | 0.12" | 0.058" | 0.02" |
| None | V0 | V1 | V1 |
| H | V0 | V0 | V1 |
| G | V0 | V0 | V0 |
| K | V0 | V0 | V0 |
| N | V0 | V0 | V0 |
| AA | V0 | V0 | V1 |
| AJ | V0 | V1 | V1 |

Note the greater efficacy of products of the instant invention and as compared to their prior art analogs, as flame retardant enhancers in ABS.

EXAMPLE 8

Evaluation of Various Coupling Agent as Water Absorption Inhibitors in Extruded Ethyl Cellulose

| Formulation: | |
| --- | --- |
| Ethyl Cellulose (Hercules Type T) | 100.0 |
| Coupling Agent (as shown) | 0.5 |
| | 100.5 |

Composite Process: Ethyl cellulose and coupling agent ball milled for four hours followed by extrusion at 230° C.

| | Properties - Extrudate, As Received: | |
| --- | --- | --- |
| Coupling Agent | 24 Hour Water Absorption ASTM D570 | 24 Hour Water Absorption ASTM D570 |
| None | 1.2 | 1.8 |
| C | 0.8 | 1.2 |
| V | 0.4 | 1.0 |
| N | 0.5 | 0.9 |
| AA | 0.9 | 1.8 |
| AG | 0.7 | 1.4 |
| AF | 0.9 | 1.8 |

EXAMPLE 9

Monoalkoxy and Neoalkoxy Titanate Viscosity Reduction Effects on Unfilled Silicon Oil Titanates @ 0.2% on silicone oil (Polydimethyl Siloxane—30,000 centistokes) LVT, Spindle #4, 6 RPM, 72° F.

Samples were drill mixed for approx. 3 minutes then let stand overnight to allow air bubbles to escape.

|  | Viscosity, cps |
|---|---|
| Control A | 40,000 |
| Control B (drill mixed) | 39,500 |
| C | 40,000 |
| V | 22,000 |
| N | 38,500 |
| K | 30,000 |
| AG | 33,500 |
| AL | 26,000 |
| AA | 39,500 |
| AJ | 26,000 |

The effect of various neoalkoxy titanates and neoalkoxy zirconates on the properties of unfilled injection molded thermoplastic resins is shown in the following examples. All evaluations were performed by tumble blending virgin resin with the indicated quantity of coupling agent (as 65% powder concentrate on precipitate silica) prior to molding at the cited temperature. After molding, the resultant specimens were equilibrated at ambient temperature (under indoor noncontrolled humidity) for 48 to 74 hours prior to physicals' evaluation. Molding equipment used in all cases was a 4 oz., 100 ton New Britain non-vented screw type molding machine and a mold having cored ss mold cavities.

All listed were to ASTM protocol. Tensile yield—D638, % Elongation—D638, Flexural Strength—D790, Flexural Modulus—D790, Notched Izod—D256, Impact Strength—D256, % Water Absorption (24 hr.)—D570. Each data point is the average of 4 to 6 individual test results.

EXAMPLE 10

EFFECT OF NEOALKOXY TITANATE AND NEOALKOXY ZIRCONATE ON THE PROPERTIES OF INJECTION MOLDED UNFILLED ABS
Resin: ABS Type - Lustron HR 850 (Monsanto)
Molding Temperature: 540° F. (Nominal) - Resin Predried

| Coupling Agent Additive | Weight % of Resin | Tensile Yield K psi | % Elongation @ Break | Flexural Strength K psi | Flexural Modulus psi × $10^4$ | Notched Izod @ R.T. ft. lb./in. | % Water Absorption @ R.T. 24 Hr. Imm. |
|---|---|---|---|---|---|---|---|
| None | — | 7.1 | 18 | 12 | 41 | 3.0 | 0.30 |
| C | 0.1 | 7.4 | 26 | 14 | 52 | 3.2 | 0.27 |
| C | 0.3 | 7.2 | 55 | 12 | 44 | 3.6 | 0.30 |
| C | 0.5 | 7.0 | 61 | 11 | 38 | 3.8 | 0.31 |
| V | 0.1 | 7.5 | 41 | 16 | 55 | 3.7 | 0.24 |
| V | 0.3 | 7.6 | 68 | 21 | 63 | 3.9 | 0.26 |
| V | 0.5 | 7.2 | 70 | 17 | 46 | 3.1 | 0.27 |
| N | 0.1 | 8.4 | 32 | 19 | 56 | 3.5 | 0.17 |
| N | 0.3 | 8.4 | 39 | 26 | 62 | 4.4 | 0.19 |
| N | 0.5 | 7.3 | 26 | 17 | 43 | 3.9 | 0.21 |
| K | 0.1 | 7.2 | 24 | 14 | 48 | 3.2 | 0.28 |
| K | 0.3 | 7.5 | 27 | 19 | 51 | 3.4 | 0.26 |
| K | 0.5 | 7.4 | 21 | 17 | 51 | 3.4 | 0.26 |
| U | 0.1 | 7.9 | 23 | 31 | 56 | 3.9 | 0.19 |
| U | 0.3 | 8.5 | 20 | 37 | 62 | 4.6 | 0.12 |
| U | 0.5 | 9.4 | 17 | 42 | 69 | 4.8 | 0.08 |
| U | 1.0 | 9.5 | 14 | 49 | 82 | 3.2 | 0.08 |
| U | 2.0 | 8.0 | 8 | 50 | 86 | 1.7 | 0.04 |
| W | 0.1 | 8.0 | 41 | 38 | 57 | 4.1 | 0.17 |
| W | 0.3 | 8.5 | 46 | 39 | 64 | 4.9 | 0.15 |
| W | 0.5 | 8.4 | 40 | 44 | 69 | 5.0 | 0.12 |
| W | 0.75 | 8.1 | 21 | 52 | 85 | 2.8 | 0.09 |
| Z1 | 0.1 | 7.7 | 19 | 16 | 51 | 3.7 | 0.24 |
| Z1 | 0.3 | 7.9 | 23 | 19 | 48 | 3.9 | 0.23 |
| Z1 | 0.5 | 7.8 | 28 | 12 | 44 | 3.8 | 0.19 |
| Z2 | 0.1 | 7.9 | 31 | 31 | 51 | 4.2 | 0.19 |
| Z2 | 0.3 | 8.3 | 39 | 30 | 43 | 4.4 | 0.17 |
| Z2 | 0.5 | 8.0 | 30 | 27 | 43 | 4.5 | 0.15 |
| Z3 | 0.1 | 7.9 | 28 | 24 | 51 | 3.9 | 0.22 |
| Z3 | 0.3 | 8.2 | 34 | 30 | 70 | 4.1 | 0.20 |
| Z3 | 0.5 | 8.0 | 37 | 28 | 62 | 4.4 | 0.21 |
| Z4 | 0.2 | 7.4 | 19 | 17 | 46 | 3.2 | 0.26 |
| Z4 | 0.3 | 7.6 | 25 | 21 | 51 | 3.9 | 0.24 |
| Z4 | 0.5 | 7.3 | 27 | 16 | 48 | 3.4 | 0.19 |
| Z5 | 0.1 | 8.2 | 34 | 42 | 63 | 4.1 | 0.18 |
| Z5 | 0.3 | 8.9 | 28 | 57 | 71 | 4.3 | 0.16 |
| Z5 | 0.5 | 9.9 | 26 | 63 | 79 | 4.2 | 0.12 |
| Z5 | 1.0 | 10.2 | 26 | 65 | 82 | 3.7 | 0.09 |
| Z5 | 2.0 | 8.6 | 10 | 41 | 53 | 3.4 | 0.08 |
| Z6 | 0.1 | 8.4 | 51 | 46 | 72 | 3.7 | 0.22 |
| Z6 | 0.3 | 8.9 | 58 | 61 | 84 | 3.9 | 0.18 |
| Z6 | 0.5 | 9.4 | 41 | 67 | 89 | 4.1 | 0.14 |
| Z6 | 0.75 | 9.7 | 33 | 59 | 91 | 4.4 | 0.06 |
| Z6 | 1.0 | 8.3 | 16 | 60 | 63 | 3.4 | 0.04 |

EXAMPLE 11

EFFECT OF NEOALKOXY TITANATE AND NEOALKOXY ZIRCONATE
ON THE PROPERTIES OF INJECTION MOLDED UNFILLED ACETAL
Resin: Acetal Type - Colcon M 270 (Celanese Corp.)
Molding Temperature: 380° F. (Nominal) - Resin Predried

| Coupling Agent Additive | Weight % of Resin | Tensile Yield K psi | % Elongation @ Break | Flexural Strength K psi | Flexural Modulus psi × $10^4$ | Notched Izod @ R.T. ft. lb./in. | % Water Absorption @ R.T. 24 Hr. Imm. |
|---|---|---|---|---|---|---|---|
| None | — | 8.8 | 40 | 13 | 38 | 1.0 | 0.22 |
| C | 0.1 | 8.9 | 54 | 15 | 51 | 1.7 | 0.22 |
| C | 0.3 | 9.0 | 59 | 19 | 55 | 2.8 | 0.24 |
| C | 0.5 | 8.9 | 67 | 19 | 51 | 1.9 | 0.27 |
| V | 0.1 | 8.9 | 61 | 17 | 42 | 2.1 | 0.21 |
| V | 0.3 | 8.8 | 69 | 18 | 39 | 2.4 | 0.19 |
| V | 0.5 | 8.4 | 76 | 14 | 27 | 2.2 | 0.17 |
| N | 0.1 | 9.4 | 61 | 20 | 44 | 2.2 | 0.21 |
| N | 0.3 | 9.9 | 64 | 20 | 47 | 2.7 | 0.17 |
| N | 0.5 | 9.0 | 72 | 16 | 36 | 2.4 | 0.16 |
| K | 0.1 | 8.4 | 37 | 12 | 31 | 0.9 | 0.19 |
| K | 0.3 | 8.1 | 28 | 10 | 30 | 0.7 | 0.16 |
| K | 0.5 | 7.7 | 24 | 9 | 26 | 0.7 | 0.15 |
| U | 0.1 | 9.2 | 43 | 17 | 43 | 1.4 | 0.24 |
| U | 0.3 | 9.5 | 54 | 21 | 47 | 2.1 | 0.27 |
| U | 0.5 | 9.7 | 41 | 24 | 54 | 2.7 | 0.19 |
| U | 1.0 | 9.4 | 38 | 20 | 62 | 2.0 | 0.16 |
| W | 0.1 | 9.6 | 49 | 17 | 58 | 1.7 | 0.12 |
| W | 0.3 | 10.4 | 46 | 24 | 74 | 2.5 | 0.09 |
| W | 0.5 | 10.6 | 42 | 38 | 82 | 3.1 | 0.03 |
| W | 1.0 | 11.1 | 37 | 37 | 88 | 2.3 | 0.03 |
| W | 2.0 | 8.6 | 16 | 26 | 62 | 0.9 | 0.03 |
| Z1 | 0.1 | 9.0 | 48 | 14 | 43 | 1.1 | 0.21 |
| Z1 | 0.3 | 9.2 | 52 | 15 | 45 | 1.4 | 0.21 |
| Z1 | 0.5 | 9.0 | 55 | 13 | 44 | 1.0 | 0.22 |
| Z2 | 0.1 | 9.4 | 51 | 16 | 36 | 1.4 | 0.17 |
| Z2 | 0.3 | 9.4 | 55 | 17 | 34 | 1.9 | 0.17 |
| Z2 | 0.5 | 9.2 | 50 | 12 | 33 | 1.9 | 0.15 |
| Z3 | 0.1 | 9.4 | 52 | 17 | 46 | 1.4 | 0.17 |
| Z3 | 0.3 | 9.7 | 61 | 21 | 53 | 2.1 | 0.14 |
| Z3 | 0.5 | 9.9 | 67 | 30 | 57 | 2.0 | 0.13 |
| Z3 | 0.75 | 9.3 | 60 | 24 | 40 | 1.7 | 0.09 |
| Z4 | 0.1 | 8.5 | 46 | 15 | 36 | 1.0 | 0.24 |
| Z4 | 0.3 | 8.5 | 49 | 13 | 34 | 0.9 | 0.21 |
| Z4 | 0.5 | 8.2 | 52 | 11 | 31 | 0.9 | 0.20 |
| Z5 | 0.1 | 9.4 | 51 | 17 | 42 | 1.4 | 0.20 |
| Z5 | 0.3 | 10.9 | 54 | 29 | 61 | 1.9 | 0.17 |
| Z5 | 0.5 | 10.6 | 56 | 34 | 66 | 1.9 | 0.17 |
| Z5 | 0.75 | 8.4 | 32 | 19 | 71 | 0.9 | 0.15 |
| Z6 | 0.1 | 10.0 | 61 | 19 | 45 | 1.4 | 0.16 |
| Z6 | 0.3 | 10.4 | 67 | 27 | 56 | 1.7 | 0.14 |
| Z6 | 0.5 | 10.7 | 72 | 29 | 62 | 1.9 | 0.14 |
| Z6 | 1.0 | 10.9 | 71 | 31 | 67 | 2.0 | 0.12 |
| Z6 | 1.5 | 10.2 | 48 | 20 | 74 | 1.0 | 0.10 |

EXAMPLE 12

EFFECT OF NEOALKOXY TITANATE AND NEOALKOXY ZIRCONATE
ON THE PROPERTIES OF INJECTION MOLDED UNFILLED ACRYLIC
Resin: Acrylic Type - Lucite 239K (DuPont)
Molding Temperature: 480° F. (Nominal) - Resin Predried

| Coupling Agent Additive | Weight % of Resin | Tensile Yield K psi | % Elongation @ Break | Flexural Strength K psi | Flexural Modulus psi × $10^4$ | Notched Izod @ R.T. ft. lb./in. | % Water Absorption @ R.T. 24 Hr. Imm |
|---|---|---|---|---|---|---|---|
| None | — | 1.2 | 5 | 15 | 26 | 0.3 | 0.27 |
| C | 0.1 | 1.4 | 17 | 17 | 29 | 0.5 | 0.22 |
| C | 0.3 | 1.5 | 23 | 20 | 30 | 0.9 | 0.21 |
| C | 0.5 | 1.2 | 28 | 18 | 25 | 1.1 | 0.18 |
| V | 0.1 | 1.3 | 19 | 16 | 31 | 0.4 | 0.22 |
| V | 0.3 | 1.5 | 24 | 24 | 30 | 0.7 | 0.22 |
| V | 0.5 | 1.4 | 27 | 23 | 26 | 0.8 | 0.20 |
| N | 0.1 | 1.5 | 16 | 20 | 22 | 0.5 | 0.17 |
| N | 0.3 | 1.7 | 31 | 23 | 29 | 0.7 | 0.15 |
| N | 0.5 | 1.6 | 26 | 24 | 28 | 0.8 | 0.12 |
| N | 0.75 | 1.5 | 28 | 21 | 20 | 0.7 | 0.09 |
| K | 0.1 | 1.4 | 13 | 21 | 38 | 0.4 | 0.22 |
| K | 0.3 | 1.7 | 28 | 24 | 43 | 0.6 | 0.21 |

-continued
EFFECT OF NEOALKOXY TITANATE AND NEOALKOXY ZIRCONATE ON THE PROPERTIES OF INJECTION MOLDED UNFILLED ACRYLIC
Resin: Acrylic Type - Lucite 239K (DuPont)
Molding Temperature: 480° F. (Nominal) - Resin Predried

| Coupling Agent Additive | Weight % of Resin | Tensile Yield K psi | % Elongation @ Break | Flexural Strength K psi | Flexural Modulus psi × $10^4$ | Notched Izod @ R.T. ft. lb./in. | % Water Absorption @ R.T. 24 Hr. Imm |
|---|---|---|---|---|---|---|---|
| K  | 0.5  | 1.3 | 34 | 20 | 27 | 0.4 | 0.22 |
| U  | 0.1  | 1.7 | 24 | 19 | 40 | 0.5 | 0.30 |
| U  | 0.3  | 2.2 | 16 | 31 | 52 | 0.7 | 0.31 |
| U  | 0.5  | 2.5 | 12 | 24 | 57 | 0.5 | 0.28 |
| U  | 0.75 | 2.0 | 9  | 20 | 48 | 0.3 | 0.24 |
| W  | 0.1  | 1.9 | 12 | 19 | 38 | 0.4 | 0.16 |
| W  | 0.3  | 2.1 | 20 | 24 | 44 | 0.5 | 0.14 |
| W  | 0.5  | 2.3 | 16 | 25 | 47 | 0.5 | 0.11 |
| W  | 0.75 | 2.0 | 11 | 19 | 28 | 0.2 | 0.08 |
| Z1 | 0.1  | 1.3 | 9  | 15 | 31 | 0.4 | 0.26 |
| Z1 | 0.3  | 1.4 | 14 | 18 | 34 | 0.5 | 0.24 |
| Z1 | 0.5  | 1.1 | 17 | 13 | 29 | 0.7 | 0.25 |
| Z2 | 0.1  | 1.2 | 23 | 16 | 30 | 0.3 | 0.24 |
| Z2 | 0.3  | 1.0 | 31 | 19 | 28 | 0.5 | 0.21 |
| Z2 | 0.5  | 1.0 | 36 | 18 | 27 | 0.5 | 0.22 |
| Z3 | 0.1  | 1.4 | 16 | 19 | 39 | 0.5 | 0.19 |
| Z3 | 0.3  | 1.7 | 23 | 24 | 35 | 0.7 | 0.17 |
| Z3 | 0.5  | 1.5 | 27 | 17 | 32 | 0.6 | 0.12 |
| Z4 | 0.1  | 1.4 | 21 | 14 | 38 | 0.5 | 0.19 |
| Z4 | 0.3  | 1.5 | 34 | 17 | 42 | 0.7 | 0.18 |
| Z4 | 0.5  | 1.3 | 29 | 16 | 31 | 0.7 | 0.18 |
| Z5 | 0.1  | 1.9 | 17 | 17 | 42 | 0.6 | 0.31 |
| Z5 | 0.3  | 2.0 | 15 | 26 | 47 | 0.7 | 0.34 |
| Z5 | 0.5  | 2.0 | 9  | 21 | 44 | 0.2 | 0.38 |
| Z6 | 0.1  | 1.7 | 11 | 21 | 38 | 0.3 | 0.16 |
| Z6 | 0.3  | 2.2 | 10 | 24 | 47 | 0.4 | 0.12 |
| Z6 | 0.5  | 2.5 | 10 | 23 | 52 | 0.4 | 0.09 |
| Z6 | 0.75 | 2.1 | 6  | 19 | 55 | 0.3 | 0.09 |

EXAMPLE 13

EFFECT OF NEOALKOXY TITANATE AND NEOALKOXY ZIRCONATE ON THE PROPERTIES OF INJECTION MOLDED UNFILLED CELLULOSE ACETATE BUTYRATE
Resin: Cellulose Acetate Butyrate (CAB)
Type: Tenite 203H3 (Eastman)
Molding Temperature: 340° F. - Resin Predried

| Coupling Agent Additive | Weight % of Resin | Tensile Strength @ Break K psi | % Elongation @ Break | Flexural Strength K psi | Flexural Modulus psi × $10^4$ | Notched Izod @ R.T. ft. lb./in. | % Water Absorption @ R.T. 24 Hr. Imm. |
|---|---|---|---|---|---|---|---|
| None | —   | 5.8 | 42 | 8.3 | 25 | 1.7 | 1.8 |
| C  | 0.1 | 5.7 | 54 | 8.4 | 27 | 1.9 | 1.4 |
| C  | 0.3 | 6.0 | 68 | 8.9 | 31 | 2.2 | 1.1 |
| C  | 0.5 | 5.5 | 72 | 8.2 | 26 | 2.3 | 0.9 |
| V  | 0.1 | 5.3 | 39 | 8.4 | 28 | 1.9 | 1.6 |
| V  | 0.3 | 5.1 | 48 | 8.5 | 25 | 2.3 | 1.4 |
| V  | 0.5 | 5.0 | 41 | 8.5 | 23 | 2.4 | 1.3 |
| N  | 0.1 | 6.2 | 55 | 8.8 | 30 | 1.9 | 0.9 |
| N  | 0.3 | 6.5 | 72 | 9.4 | 33 | 2.6 | 0.9 |
| N  | 0.5 | 6.1 | 70 | 9.0 | 24 | 2.3 | 0.8 |
| K  | 0.1 | 6.4 | 48 | 8.7 | 38 | 1.9 | 1.6 |
| K  | 0.3 | 6.2 | 62 | 9.2 | 41 | 1.7 | 1.5 |
| K  | 0.5 | 6.0 | 70 | 8.1 | 27 | 1.5 | 1.5 |
| U  | 0.1 | 5.9 | 54 | 8.4 | 26 | 2.0 | 1.9 |
| U  | 0.3 | 6.3 | 71 | 8.9 | 31 | 2.6 | 1.7 |
| U  | 0.5 | 6.3 | 74 | 8.2 | 30 | 2.1 | 1.4 |
| W  | 0.1 | 6.1 | 58 | 8.4 | 31 | 2.0 | 1.4 |
| W  | 0.3 | 6.5 | 79 | 8.9 | 52 | 2.5 | 1.2 |
| W  | 0.5 | 6.2 | 67 | 8.9 | 55 | 2.2 | 0.9 |
| Z1 | 0.1 | 5.9 | 49 | 8.2 | 34 | 1.9 | 1.6 |
| Z1 | 0.3 | 5.8 | 50 | 8.1 | 30 | 1.8 | 1.4 |
| Z1 | 0.5 | 5.6 | 54 | 8.1 | 27 | 1.9 | 1.0 |
| Z2 | 0.1 | 6.0 | 50 | 8.4 | 27 | 1.9 | 1.2 |
| Z2 | 0.3 | 6.2 | 59 | 8.5 | 30 | 2.2 | 1.1 |
| Z2 | 0.5 | 5.8 | 63 | 8.2 | 24 | 2.3 | 1.1 |
| Z3 | 0.1 | 6.1 | 48 | 8.4 | 30 | 1.8 | 1.7 |
| Z3 | 0.3 | 6.4 | 67 | 9.3 | 32 | 1.9 | 1.5 |
| Z3 | 0.5 | 6.0 | 69 | 9.1 | 28 | 1.8 | 1.5 |
| Z4 | 0.1 | 5.9 | 48 | 8.4 | 29 | 1.8 | 1.8 |

-continued

EFFECT OF NEOALKOXY TITANATE AND NEOALKOXY ZIRCONATE
ON THE PROPERTIES OF INJECTION MOLDED UNFILLED
CELLULOSE ACETATE BUTYRATE
Resin: Cellulose Acetate Butyrate (CAB)
Type: Tenite 203H3 (Eastman)
Molding Temperature: 340° F. - Resin Predried

| Coupling Agent Additive | Weight % of Resin | Tensile Strength @ Break K psi | % Elongation @ Break | Flexural Strength K psi | Flexural Modulus psi × $10^4$ | Notched Izod @ R.T. ft. lb./in. | % Water Absorption @ R.T. 24 Hr. Imm. |
|---|---|---|---|---|---|---|---|
| Z4 | 0.3 | 6.2 | 54 | 8.7 | 32 | 1.7 | 1.8 |
| Z4 | 0.5 | 6.0 | 55 | 8.2 | 27 | 1.5 | 1.7 |
| Z5 | 0.1 | 6.2 | 51 | 8.2 | 31 | 2.0 | 1.6 |
| Z5 | 0.3 | 6.7 | 62 | 8.9 | 38 | 2.5 | 1.5 |
| Z5 | 0.5 | 6.1 | 65 | 8.5 | 42 | 2.1 | 1.4 |
| Z6 | 0.1 | 6.1 | 58 | 9.1 | 42 | 2.2 | 0.9 |
| Z6 | 0.3 | 7.0 | 42 | 9.7 | 59 | 2.6 | 0.8 |
| Z6 | 0.5 | 6.4 | 37 | 9.2 | 53 | 2.1 | 0.8 |

EXAMPLE 14

EFFECT OF NEOALKOXY TITANATE AND NEOALKOXY ZIRCONATE
ON THE PROPERTIES OF INJECTION MOLDED UNFILLED NYLON 6
Resin: Nylon 6
Type: Capron 820L (Allied)
Molding Temperature: 460° F. (Nominal) - Resin Predried

| Coupling Agent Additive | Weight % of Resin | Tensile Yield K psi | % Elongation @ Break | Flexural Strength K psi | Flexural Modulus psi × $10^4$ | Notched Izod @ R.T. ft. lb./in. | % Water Absorption @ R.T. 24 Hr. Imm. |
|---|---|---|---|---|---|---|---|
| None | — | 18 | 60 | 16 | 41 | 1.0 | 1.6 |
| C | 0.1 | 17 | 75 | 18 | 47 | 1.4 | 1.1 |
| C | 0.3 | 16 | 82 | 20 | 43 | 1.7 | 0.8 |
| C | 0.5 | 14 | 90 | 17 | 36 | 1.2 | 0.7 |
| V | 0.1 | 17 | 67 | 18 | 42 | 1.2 | 1.2 |
| V | 0.3 | 19 | 70 | 17 | 40 | 1.3 | 1.3 |
| V | 0.5 | 18 | 68 | 17 | 35 | 1.0 | 1.5 |
| N | 0.1 | 19 | 72 | 20 | 44 | 1.4 | 1.1 |
| N | 0.3 | 24 | 81 | 25 | 52 | 1.8 | 0.9 |
| N | 0.5 | 22 | 83 | 21 | 38 | 1.6 | 0.8 |
| K | 0.1 | 18 | 72 | 16 | 43 | 1.2 | 1.4 |
| K | 0.3 | 19 | 75 | 15 | 40 | 1.5 | 1.4 |
| K | 0.5 | 16 | 68 | 15 | 34 | 1.2 | 1.2 |
| U | 0.1 | 20 | 71 | 20 | 50 | 1.1 | 1.5 |
| U | 0.3 | 23 | 78 | 24 | 54 | 1.5 | 1.3 |
| U | 0.5 | 25 | 75 | 27 | 59 | 1.5 | 1.3 |
| U | 0.75 | 24 | 70 | 22 | 58 | 1.2 | 1.4 |
| W | 0.1 | 20 | 62 | 18 | 62 | 1.4 | 0.9 |
| W | 0.3 | 25 | 67 | 22 | 67 | 1.7 | 0.7 |
| W | 0.5 | 29 | 60 | 27 | 71 | 1.9 | 0.7 |
| W | 0.75 | 30 | 58 | 29 | 68 | 2.0 | 0.6 |
| W | 1.0 | 27 | 46 | 31 | 72 | 1.3 | 0.4 |
| Z1 | 0.1 | 16 | 72 | 17 | 42 | 1.1 | 1.1 |
| Z1 | 0.3 | 16 | 74 | 19 | 44 | 1.4 | 1.0 |
| Z1 | 0.5 | 15 | 77 | 16 | 38 | 1.5 | 1.0 |
| Z2 | 0.1 | 17 | 64 | 17 | 40 | 1.0 | 1.4 |
| Z2 | 0.3 | 16 | 69 | 20 | 41 | 1.3 | 1.3 |
| Z2 | 0.5 | 15 | 67 | 18 | 38 | 1.4 | 1.3 |
| Z3 | 0.1 | 17 | 70 | 18 | 44 | 1.1 | 1.0 |
| Z3 | 0.3 | 19 | 78 | 22 | 49 | 1.7 | 1.0 |
| Z3 | 0.5 | 15 | 82 | 22 | 42 | 1.4 | 0.9 |
| Z4 | 0.1 | 18 | 70 | 16 | 41 | 1.1 | 1.4 |
| Z4 | 0.3 | 23 | 77 | 19 | 48 | 1.4 | 1.2 |
| Z4 | 0.5 | 23 | 71 | 15 | 44 | 1.3 | 1.2 |
| Z5 | 0.1 | 18 | 62 | 18 | 49 | 1.2 | 1.2 |
| Z5 | 0.3 | 23 | 70 | 22 | 54 | 1.5 | 1.0 |
| Z5 | 0.5 | 27 | 79 | 25 | 63 | 1.7 | 1.0 |
| Z5 | 0.75 | 30 | 80 | 28 | 70 | 1.7 | 0.9 |
| Z5 | 1.0 | 28 | 74 | 22 | 72 | 1.5 | 0.7 |
| Z6 | 0.1 | 20 | 70 | 20 | 48 | 1.4 | 0.9 |
| Z6 | 0.3 | 24 | 77 | 24 | 54 | 1.9 | 0.9 |
| Z6 | 0.5 | 28 | 84 | 27 | 57 | 2.2 | 0.8 |
| Z6 | 0.75 | 30 | 85 | 30 | 61 | 2.3 | 0.7 |
| Z6 | 1.0 | 31 | 60 | 28 | 67 | 1.1 | 0.5 |

EXAMPLE 15

EFFECT OF NEOALKOXY TITANATE AND NEOALKOXY ZIRCONATE ON THE PROPERTIES OF INJECTION MOLDED UNFILLED POLYCARBONATE

Resin: Plolycarbonate
Type: Lexan PPC (General Electric)
Molding Temperature: 560° F. - Resin Predried

| Coupling Agent Additive | Weight % of Resin | Tensile Yield K psi | % Elongation @ Bread | Flexural Strength K psi | Flexural Modulus psi × $10^4$ | Notched Izod @ R.T. ft. lb./in. | % Water Absorption @ R.T. 24 Hr. Imm. |
|---|---|---|---|---|---|---|---|
| None | — | 9.7 | 65 | 13 | 33 | 6.0 | 0.20 |
| C | 0.1 | 9.7 | 68 | 14 | 31 | 6.1 | 0.17 |
| C | 0.3 | 9.5 | 72 | 15 | 30 | 6.4 | 0.15 |
| C | 0.5 | 9.3 | 76 | 14 | 30 | 6.3 | 0.13 |
| V | 0.1 | 9.9 | 72 | 15 | 36 | 6.3 | 0.19 |
| V | 0.3 | 10.4 | 79 | 19 | 47 | 6.9 | 0.17 |
| V | 0.5 | 10.8 | 83 | 20 | 49 | 7.1 | 0.16 |
| V | 0.75 | 10.4 | 87 | 18 | 44 | 7.2 | 0.14 |
| N | 0.1 | 9.9 | 80 | 15 | 39 | 6.9 | 0.17 |
| N | 0.3 | 10.5 | 89 | 27 | 41 | 6.9 | 0.14 |
| N | 0.5 | 10.2 | 86 | 27 | 40 | 6.9 | 0.11 |
| N | 0.75 | 10.1 | 85 | 23 | 37 | 6.7 | 0.09 |
| K | 0.1 | 10.1 | 82 | 19 | 36 | 6.2 | 0.19 |
| K | 0.3 | 10.4 | 91 | 21 | 38 | 6.7 | 0.17 |
| K | 0.5 | 9.8 | 86 | 20 | 33 | 6.1 | 0.16 |
| U | 0.1 | 10.4 | 80 | 17 | 42 | 6.0 | 0.17 |
| U | 0.3 | 11.1 | 87 | 22 | 45 | 6.0 | 0.15 |
| U | 0.5 | 10.3 | 68 | 20 | 38 | 6.1 | 0.12 |
| W | 0.1 | 10.0 | 82 | 15 | 42 | 6.4 | 0.19 |
| W | 0.3 | 11.4 | 91 | 19 | 47 | 7.1 | 0.17 |
| W | 0.5 | 11.7 | 94 | 24 | 54 | 8.3 | 0.16 |
| W | 0.75 | 11.7 | 83 | 25 | 59 | 8.6 | 0.14 |
| W | 1.0 | 11.2 | 80 | 25 | 62 | 8.0 | 0.12 |
| Z1 | 0.1 | 9.7 | 69 | 13 | 35 | 6.2 | 0.17 |
| Z1 | 0.3 | 9.5 | 78 | 16 | 34 | 6.7 | 0.15 |
| Z1 | 0.5 | 9.4 | 83 | 12 | 30 | 6.8 | 0.12 |
| Z2 | 0.1 | 9.9 | 72 | 14 | 35 | 6.4 | 0.18 |
| Z2 | 0.3 | 10.2 | 77 | 16 | 39 | 6.7 | 0.16 |
| Z2 | 0.5 | 10.0 | 78 | 15 | 32 | 6.2 | 0.15 |
| Z3 | 0.1 | 10.0 | 65 | 14 | 38 | 6.8 | 0.18 |
| Z3 | 0.3 | 10.4 | 69 | 19 | 42 | 7.4 | 0.16 |
| Z3 | 0.5 | 10.2 | 73 | 14 | 34 | 7.9 | 0.14 |
| Z4 | 0.1 | 9.7 | 67 | 14 | 34 | 6.7 | 0.18 |
| Z4 | 0.3 | 9.7 | 67 | 17 | 36 | 7.2 | 0.17 |
| Z4 | 0.5 | 9.5 | 65 | 13 | 32 | 7.5 | 0.18 |
| Z5 | 0.1 | 9.9 | 67 | 14 | 41 | 6.7 | 0.21 |
| Z5 | 0.3 | 10.3 | 73 | 19 | 47 | 6.8 | 0.20 |
| Z5 | 0.5 | 10.0 | 72 | 15 | 48 | 7.0 | 0.20 |
| Z6 | 0.1 | 10.1 | 62 | 15 | 40 | 7.1 | 0.16 |
| Z6 | 0.3 | 10.4 | 69 | 19 | 47 | 7.4 | 0.10 |
| Z6 | 0.5 | 10.9 | 74 | 25 | 53 | 7.9 | 0.08 |
| Z6 | 0.75 | 11.3 | 78 | 23 | 5.9 | 8.0 | 0.07 |
| Z6 | 1.0 | 10.5 | 70 | 21 | 58 | 7.3 | 0.07 |

EXAMPLE 16

EFFECT OF NEOALKOXY TITANATE AND NEOALKOXY ZIRCONATE ON THE PROPERTIES OF INJECTION MOLDED UNFILLED POLYPROPYLENE

Resin: Polypropylene
Type: Bapolan 4063N (Bamberger Polymers)
Molding Temperature: 480° F.

| Coupling Agent Additive | Weight % of Resin | Tensile Strength @ Yield K psi | % Elongation @ Break | Flexural Strength K psi | Flexural Modulus psi × $10^4$ | Notched Izod @ R.T. ft. lb./in. |
|---|---|---|---|---|---|---|
| None | — | 4.9 | 120 | — | 21 | 0.7 |
| C | 0.1 | 5.0 | 137 | — | 22 | 0.8 |
| C | 0.3 | 5.2 | 147 | — | 24 | 0.9 |
| C | 0.5 | 5.5 | 152 | — | 21 | 1.1 |
| C | 0.75 | 5.0 | 151 | — | 19 | 1.0 |
| V | 0.1 | 5.4 | 129 | — | 24 | 1.0 |
| V | 0.3 | 5.8 | 140 | — | 28 | 1.4 |
| V | 0.5 | 5.2 | 116 | — | 23 | 1.5 |
| N | 0.1 | 5.4 | 127 | — | 24 | 0.9 |
| N | 0.3 | 5.7 | 142 | — | 26 | 1.1 |

-continued

EFFECT OF NEOALKOXY TITANATE AND NEOALKOXY ZIRCONATE ON THE PROPERTIES OF INJECTION MOLDED UNFILLED POLYPROPYLENE
Resin: Polypropylene
Type: Bapolan 4063N (Bamberger Polymers)
Molding Temperature: 480° F.

| Coupling Agent Additive | Weight % of Resin | Tensile Strength @ Yield K psi | % Elongation @ Break | Flexural Strength K psi | Flexural Modulus psi × $10^4$ | Notched Izod @ R.T. ft. lb./in. |
|---|---|---|---|---|---|---|
| N | 0.5 | 5.6 | 148 | — | 22 | 1.4 |
| N | 0.75 | 5.2 | 139 | — | 21 | 1.1 |
| U | 0.1 | 5.2 | 124 | — | 23 | 1.0 |
| U | 0.3 | | | exudes | | |
| W | 0.1 | 5.2 | 125 | — | 24 | 1.1 |
| W | 0.3 | 5.5 | 122 | — | 21 | 1.3 |
| W | 0.5 | | | exudes | | |
| Z1 | 0.1 | 5.2 | 137 | — | 26 | 1.2 |
| Z1 | 0.3 | 6.1 | 152 | — | 34 | 1.5 |
| Z1 | 0.5 | 5.4 | 141 | — | 25 | 1.6 |
| Z2 | 0.1 | 5.0 | 140 | — | 23 | 1.0 |
| Z2 | 0.3 | 5.7 | 156 | — | 25 | 1.1 |
| Z2 | 0.5 | 5.5 | 142 | — | 21 | 1.2 |
| Z3 | 0.1 | 5.4 | 142 | — | 24 | 1.1 |
| Z3 | 0.3 | 5.9 | 157 | — | 26 | 1.4 |
| Z3 | 0.5 | 6.2 | 165 | — | 24 | 1.6 |
| Z3 | 0.75 | 6.0 | 149 | — | 22 | 1.5 |
| Z4 | 0.1 | 5.2 | 127 | — | 21 | 1.0 |
| Z4 | 0.3 | 5.3 | 129 | — | 20 | 1.1 |
| Z4 | 0.5 | 5.1 | 121 | — | 20 | 1.2 |
| Z5 | 0.1 | 5.0 | 124 | — | 22 | 1.1 |
| Z5 | 0.3 | 5.2 | 128 | — | 24 | 1.1 |
| Z5 | 0.5 | | | exudes | | |
| Z6 | 0.1 | 5.2 | 122 | — | 20 | 1.0 |
| Z6 | 0.3 | 5.4 | 127 | — | 20 | 1.2 |
| Z6 | 0.5 | | | exudes | | |

EXAMPLE 17

EFFECT OF NEOALKOXY TITANATE AND NEOALKOXY ZIRCONATE ON THE PROPERTIES OF INJECTION MOLDED UNFILLED HDPE
Resin: HDPE
Yype: 403F3 (Amoco)
Molding Temperature: 490° F.

| Coupling Agent Additive | Weight % of Resin | Tensile Strength @ Break K psi | % Elongation @ Break | Flexural Strength K psi | Flexural Modulus psi × $10^4$ | Notched Izod @ R.T. ft. lb./in. |
|---|---|---|---|---|---|---|
| None | — | 4.5 | 820 | — | 19 | 6.0 |
| C | 0.1 | 4.9 | 880 | — | 22 | 6.2 |
| C | 0.3 | 4.7 | 940 | — | 20 | 6.9 |
| C | 0.5 | 4.4 | 1000 | — | 17 | 7.1 |
| V | 0.1 | 4.6 | 840 | — | 22 | 6.2 |
| V | 0.3 | 5.0 | 960 | — | 27 | 6.7 |
| V | 0.5 | 4.5 | 1000 | — | 21 | 5.9 |
| N | 0.1 | 4.9 | 910 | — | 27 | 6.2 |
| N | 0.3 | 5.4 | 1000 | — | 24 | 6.7 |
| N | 0.5 | 5.0 | 1000 | — | 21 | 7.0 |
| K | 0.1 | 4.6 | 840 | — | 22 | 6.1 |
| K | 0.3 | 4.9 | 930 | — | 25 | 6.3 |
| K | 0.5 | 4.5 | 950 | — | 21 | 6.3 |
| U | 0.1 | 4.4 | 800 | — | 21 | 6.0 |
| U | 0.3 | 4.5 | 820 | — | 18 | 5.8 |
| U | 0.5 (sl exudes) | 4.1 | 890 | — | 15 | 5.7 |
| W | 0.1 | 4.3 | 800 | — | 19 | 6.0 |
| W | 0.3 | 4.1 | 780 | — | 17 | 6.1 |
| W | 0.5 | 4.0 | 750 | — | 16 | 6.1 |
| Z1 | 0.1 | 4.6 | 840 | — | 22 | 6.4 |
| Z1 | 0.3 | 4.9 | 930 | — | 24 | 6.5 |
| Z1 | 0.5 | 5.4 | 1000 | — | 28 | 6.7 |
| Z1 | 0.75 | 5.2 | 1000 | — | 21 | 6.9 |
| Z2 | 0.1 | 4.7 | 820 | — | 23 | 6.0 |
| Z2 | 0.3 | 4.9 | 870 | — | 25 | 6.1 |
| Z2 | 0.5 | 4.4 | 760 | — | 22 | 6.0 |
| Z3 | 0.1 | 4.7 | 830 | — | 20 | 6.3 |
| Z3 | 0.3 | 4.9 | 870 | — | 20 | 6.9 |
| Z3 | 0.5 | 4.8 | 910 | — | 18 | 7.0 |
| Z5 | 0.3 | 4.4 | 790 | — | 18 | 6.1 |

-continued

EFFECT OF NEOALKOXY TITANATE AND NEOALKOXY ZIRCONATE ON THE PROPERTIES OF INJECTION MOLDED UNFILLED HDPE
Resin: HDPE
Yype: 403F3 (Amoco)
Molding Temperature: 490° F.

| Coupling Agent Additive | Weight % of Resin | Tensile Strength @ Break K psi | % Elongation @ Break | Flexural Strength K psi | Flexural Modulus psi × $10^4$ | Notched Izod @ R.T. ft. lb./in. |
|---|---|---|---|---|---|---|
| Z5 | 0.5 (sl exudes) | 4.1 | 740 | — | 16 | 5.9 |
| Z6 | 0.1 | 4.7 | 820 | — | 23 | 6.0 |
| Z6 | 0.3 | 4.9 | 890 | — | 22 | 6.5 |
| Z6 | 0.5 | 4.5 | 940 | — | 18 | 6.1 |

EXAMPLE 18

EFFECT OF NEOALKOXY TITANATE AND NEOALKOXY ZIRCONATE ON THE PROPERTIES OF INJECTION MOLDED UNFILLED POLYBUTYLENE TERPHTHALATE
Resin: Polybutylene Terphthalate
Type: Gafite 1602 (GAF Corp.)
Molding Temperature: 480° F. - Resin Predried

| Coupling Agent Additive | Weight % of Resin | Tensile Strength @ Break K psi | % Elongation @ Break | Flexural Strength K psi | Flexural Modulus psi × $10^4$ | Notched Izod @ R.T. ft. lb./in. | % Water Absorption @ R.T. 24 Hr. Imm. |
|---|---|---|---|---|---|---|---|
| None | — | 8.7 | 200 | 12 | 34 | 1.0 | 0.08 |
| C | 0.1 | 8.9 | 240 | 13 | 29 | 1.2 | 0.06 |
| C | 0.3 | 8.9 | 275 | 11 | 26 | 1.3 | 0.04 |
| C | 0.5 | 8.6 | 290 | 10 | 24 | 1.3 | 0.03 |
| V | 0.1 | 9.2 | 240 | 13 | 39 | 1.3 | 0.05 |
| V | 0.3 | 9.6 | 270 | 17 | 43 | 1.6 | 0.04 |
| V | 0.5 | 9.4 | 275 | 15 | 41 | 1.2 | 0.04 |
| N | 0.1 | 9.0 | 230 | 13 | 40 | 1.1 | 0.06 |
| N | 0.3 | 9.6 | 250 | 17 | 49 | 1.7 | 0.03 |
| N | 0.5 | 9.2 | 240 | 11 | 42 | 1.5 | 0.03 |
| K | 0.1 | 8.8 | 220 | 13 | 38 | 1.2 | 0.07 |
| K | 0.3 | 8.8 | 290 | 14 | 42 | 1.2 | 0.05 |
| K | 0.5 | 8.6 | 270 | 11 | 42 | 1.0 | 0.05 |
| U | 0.1 | 9.0 | 220 | 14 | 39 | 1.2 | 0.09 |
| U | 0.3 | 9.4 | 230 | 16 | 44 | 1.3 | 0.10 |
| U | 0.5 | 9.9 | 255 | 19 | 49 | 1.6 | 0.07 |
| U | 0.75 | 10.2 | 235 | 22 | 56 | 1.4 | 0.05 |
| U | 1.0 | 8.7 | 180 | 12 | 62 | 1.1 | 0.03 |
| W | 0.1 | 9.1 | 230 | 13 | 38 | 1.2 | 0.05 |
| W | 0.3 | 9.5 | 270 | 16 | 43 | 1.7 | 0.03 |
| W | 0.5 | 9.9 | 290 | 17 | 47 | 1.7 | 0.02 |
| W | 0.75 | 10.4 | 330 | 19 | 56 | 1.5 | 0.02 |
| W | 1.0 | 9.1 | 210 | 13 | 58 | 1.1 | 0.02 |
| Z1 | 0.1 | 8.8 | 210 | 14 | 37 | 1.0 | 0.07 |
| Z1 | 0.3 | 8.8 | 230 | 12 | 32 | 1.1 | 0.07 |
| Z1 | 0.5 | 8.6 | 240 | 11 | 31 | 1.1 | 0.05 |
| Z2 | 0.1 | 8.7 | 260 | 14 | 42 | 1.0 | 0.08 |
| Z2 | 0.3 | 8.9 | 310 | 15 | 49 | 1.1 | 0.06 |
| Z2 | 0.5 | 8.2 | 280 | 12 | 33 | 1.2 | 0.05 |
| Z5 | 0.1 | 8.9 | 320 | 15 | 37 | 1.1 | 0.08 |
| Z5 | 0.3 | 9.4 | 330 | 19 | 47 | 1.3 | 0.08 |
| Z5 | 0.5 | 9.7 | 300 | 20 | 48 | 1.2 | 0.07 |
| Z5 | 0.75 | 9.1 | 280 | 17 | 50 | 1.0 | 0.07 |
| Z6 | 0.1 | 9.1 | 290 | 18 | 41 | 1.1 | 0.06 |
| Z6 | 0.3 | 9.4 | 320 | 19 | 43 | 1.0 | 0.06 |
| Z6 | 0.5 | 9.9 | 330 | 23 | 48 | 1.0 | 0.04 |
| Z6 | 0.75 | 9.6 | 350 | 21 | 46 | 1.1 | 0.03 |

EXAMPLE 19

EFFECT OF NEOALKOXY TITANATE AND NEOALKOXY ZIRCONATE
ON THE PROPERTIES OF UNJECTION MOLDED
UNFILLED POLYPHENYLENE OXIDE
Resin: Polyphenylene Oxide
Type: Noryl N300 (General Electric)
Molding Temperature: 550° F.

| Coupling Agent Additive | Weight % of Resin | Tensile Yield K psi | % Elongation @ Break | Flexural Strength K psi | Flexural Modulus psi × $10^4$ | Notched Izod @ R.T. ft. lb./in. | % Water Absorption @ R.T. 24 Hr. Imm. |
|---|---|---|---|---|---|---|---|
| None | — | 11 | 48 | 35 | 35 | 10 | 0.10 |
| C | 0.1 | 11 | 52 | 36 | 34 | 11 | 0.08 |
| C | 0.3 | 10 | 57 | 35 | 32 | 11 | 0.07 |
| C | 0.5 | 9 | 61 | 33 | 30 | 10 | 0.06 |
| V | 0.1 | 11 | 54 | 39 | 41 | 12 | 0.09 |
| V | 0.3 | 14 | 68 | 46 | 42 | 14 | 0.08 |
| V | 0.5 | 13 | 66 | 42 | 35 | 11 | 0.06 |
| N | 0.1 | 11 | 49 | 36 | 35 | 11 | 0.08 |
| N | 0.3 | 12 | 50 | 38 | 39 | 13 | 0.07 |
| N | 0.5 | 11 | 52 | 35 | 34 | 11 | 0.07 |
| K | 0.1 | 12 | 49 | 38 | 39 | 12 | 0.08 |
| K | 0.3 | 13 | 60 | 42 | 44 | 14 | 0.07 |
| K | 0.5 | 11 | 63 | 40 | 35 | 11 | 0.07 |
| U | 0.1 | 14 | 48 | 38 | 42 | 13 | 0.09 |
| U | 0.3 | 17 | 46 | 44 | 47 | 14 | 0.08 |
| U | 0.5 | 13 | 43 | 41 | 45 | 11 | 0.08 |
| W | 0.1 | 13 | 57 | 39 | 39 | 12 | 0.07 |
| W | 0.3 | 15 | 63 | 42 | 44 | 14 | 0.06 |
| W | 0.5 | 17 | 71 | 48 | 48 | 17 | 0.04 |
| W | 0.75 | 12 | 72 | 42 | 47 | 13 | 0.03 |
| Z1 | 0.1 | 11 | 53 | 35 | 36 | 11 | 0.07 |
| Z1 | 0.3 | 10 | 49 | 37 | 35 | 11 | 0.07 |
| Z1 | 0.5 | 8 | 50 | 33 | 32 | 10 | 0.05 |
| Z2 | 0.1 | 11 | 58 | 37 | 39 | 12 | 0.08 |
| Z2 | 0.3 | 13 | 63 | 43 | 41 | 13 | 0.07 |
| Z2 | 0.5 | 10 | 59 | 35 | 34 | 11 | 0.07 |
| Z3 | 0.1 | 11 | 54 | 39 | 37 | 12 | 0.08 |
| Z3 | 0.3 | 14 | 57 | 43 | 35 | 14 | 0.06 |
| Z3 | 0.5 | 10 | 58 | 41 | 33 | 17 | 0.05 |
| Z5 | 0.1 | 11 | 52 | 39 | 37 | 12 | 0.08 |
| Z5 | 0.3 | 12 | 57 | 45 | 48 | 15 | 0.08 |
| Z5 | 0.5 | 12 | 61 | 40 | 51 | 16 | 0.08 |
| Z6 | 0.1 | 11 | 53 | 41 | 40 | 11 | 0.07 |
| Z6 | 0.3 | 14 | 68 | 45 | 46 | 14 | 0.05 |
| Z6 | 0.5 | 18 | 72 | 48 | 54 | 17 | 0.04 |
| Z6 | 0.75 | 12 | 59 | 43 | 43 | 17 | 0.02 |

EXAMPLE 20

EFFECT OF NEOALKOXY TITANATE AND NEOALKOXY ZIRCONATE
ON THE PROPERTIES OF UNJECTION MOLDED
UNFILLED POLYSTYRENE
Resin: Polystyrene
Type: Dylak 378 (ARCO Chemical)
Molding Temperature: 470° F.

| Coupling Agent Additive | Weight % of Resin | Tensile Yield K psi | % Elongation @ Break | Flexural Strength K psi | Flexural Modulus psi × $10^4$ | Notched Izod @ R.T. ft. lb./in. |
|---|---|---|---|---|---|---|
| None | — | 5.1 | 10 | 9.5 | 37 | 2.5 |
| C | 0.1 | 5.2 | 17 | 9.9 | 35 | 2.7 |
| C | 0.3 | 5.7 | 23 | 10.4 | 33 | 3.4 |
| C | 0.5 | 5.3 | 19 | 10.0 | 30 | 3.7 |
| V | 0.1 | 5.0 | 17 | 9.9 | 39 | 2.9 |
| V | 0.3 | 5.4 | 38 | 10.7 | 42 | 3.4 |
| V | 0.5 | 5.2 | 26 | 10.4 | 33 | 4.1 |
| N | 0.1 | 5.5 | 42 | 9.5 | 39 | 3.2 |
| N | 0.3 | 5.9 | 51 | 9.9 | 37 | 3.7 |
| N | 0.5 | 5.2 | 57 | 9.4 | 35 | 3.8 |
| U | 0.1 | 5.2 | 13 | 9.4 | 33 | 2.6 |
| U | 0.3 | 5.3 | 14 | 9.5 | 31 | 2.6 |
| U | 0.5 | | | exudes | | |
| W | 0.1 | 5.2 | 14 | 9.9 | 41 | 3.0 |
| W | 0.3 | 5.5 | 27 | 10.8 | 43 | 3.6 |
| W | 0.5 | 5.2 | 31 | 10.2 | 37 | 2.9 |
| Z1 | 0.1 | 5.0 | 13 | 9.5 | 35 | 2.7 |
| Z1 | 0.3 | 4.8 | 14 | 9.4 | 32 | 2.9 |

-continued

EFFECT OF NEOALKOXY TITANATE AND NEOALKOXY ZIRCONATE ON THE PROPERTIES OF UNJECTION MOLDED UNFILLED POLYSTYRENE
Resin: Polystyrene*
Type: Dylak 378 (ARCO Chemical)
Molding Temperature: 470° F.

| Coupling Agent Additive | Weight % of Resin | Tensile Yield K psi | % Elongation @ Break | Flexural Strength K psi | Flexural Modulus psi × 10⁴ | Notched Izod @ R.T. ft. lb./in. |
|---|---|---|---|---|---|---|
| Z1 | 0.5 | 4.6 | 12 | 9.2 | 29 | 2.9 |
| Z2 | 0.1 | 5.0 | 13 | 9.5 | 37 | 2.7 |
| Z2 | 0.3 | 5.4 | 17 | 9.9 | 41 | 3.1 |
| Z2 | 0.5 | 5.0 | 20 | 9.4 | 36 | 3.3 |
| Z3 | 0.1 | 5.3 | 14 | 9.7 | 37 | 2.6 |
| Z3 | 0.3 | 5.8 | 17 | 10.3 | 41 | 2.9 |
| Z3 | 0.5 | 5.1 | 12 | 10.0 | 36 | 3.1 |
| Z5 | 0.1 | 5.0 | 11 | 9.6 | 35 | 2.4 |
| Z5 | 0.3 | 5.1 | 12 | 9.4 | 33 | 2.2 |
| Z5 | 0.5 | 4.9 | 10 | 9.1 | 30 | 2.4 |
| Z6 | 0.1 | 5.3 | 16 | 9.8 | 36 | 2.6 |
| Z6 | 0.3 | 5.7 | 31 | 10.6 | 41 | 3.1 |
| Z6 | 0.5 | 5.8 | 37 | 10.9 | 43 | 3.4 |
| Z6 | 0.75 | 4.9 | 37 | 10.4 | 37 | 3.0 |

| Code | Chemical Description |
|---|---|
| C | 2,2(bis 2 propenolatomethyl) butanolato, trineodecanoyl titanate |
| V | 2,2(bis 2 propenolatomethyl) butanolato, dodecylbenzenesulfonyl titanate |
| N | 2,2(bis 2 propenolatomethyl) butanolato, tri(dioctylphosphato) titanate |
| K | 2,2(bis 2 propenolatomethyl) butanolato, tri(dioctylpyrophosphato) titanate |
| U | 2,2(bis 2 propenolatomethyl) butanolato, tri(N ethylaminoethylamino) titanate |
| W | 2,2(bis 2 propenolatomethyl) butanolato, tri(m-amino)-phenyltitanate |
| Z1 | 2,2 (bis 2 propenolatomethyl) butanolato, trineodecanoyl zirconate |
| Z2 | 2,2(bis 2 propenolatomethyl) butanolato, dodecylbenzenesulfonyl zirconate |
| Z3 | 2,2(bis 2 propenolatomethyl) butanolato, tri(dioctylphosphato) zirconate |
| Z4 | 2,2(bis 2 propenolatomethyl) butanolato, tri(dioctylpyrophosphato) zirconate |
| Z5 | 2,2(bis 2 propenolatomethyl) butanolato, tri(N ethylaminoethylamino) zirconate |
| Z6 | 2,2(bis 2 propenolatomethyl) butanolato, tri(m-amino)-phenyl zirconate |

We claim:

1. A process for repolymerizing a polymeric material which comprises admixing said polymeric material with from 0.005 to 5 wt. % of a neoalkoxy compound having the formula:

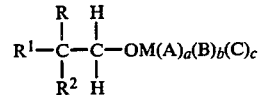

wherein M is titanium or zirconium, R, $R^1$ and $R^2$ are each a monovalent alkyl, alkenyl, alkynyl, aralkyl, aryl or alkaryl group having up to 20 carbon atoms or a halogen or ether substituted derivative thereof, and, in addition, $R^2$ may also be an oxy derivative or an ether substituted oxy derivative of said groups; A, B, and C are each a monovalent aroxy, thioaroxy, diester phosphate, diester pyrophosphate, oxyalkylamino, sulfonyl or carboxyl containing up to 30 carbon atoms; and $a+b+c=3$.

2. The process of claim 1 wherein the polymeric material is a polyalkylene terephthalate.

3. The process of claim 2 wherein the polymeric material is an admixture of polybutylene terephthalate and polyethylene terephthalate.

4. The process of claim 1 wherein the polymeric material is polyphenylene oxide.

5. The process of claim 1 wherein the polymeric material is polyurethane.

* * * * *